US007195879B2

(12) United States Patent
Dubin et al.

(10) Patent No.: US 7,195,879 B2
(45) Date of Patent: Mar. 27, 2007

(54) METHOD FOR IDENTIFYING MODULATORS OF $NA_V$ ION CHANNELS

(75) Inventors: Adrienne Dubin, San Diego, CA (US);
Sandra Chaplan, San Diego, CA (US);
Sean Brown, Encinitas, CA (US);
Edward Kaftan, Mount Prospect, IL (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/121,759

(22) Filed: Apr. 12, 2002

(65) Prior Publication Data

US 2003/0194751 A1   Oct. 16, 2003

(51) Int. Cl.
*G01N 33/53* (2006.01)
*C12N 5/00* (2006.01)
*C07D 239/00* (2006.01)
*C07C 69/00* (2006.01)

(52) U.S. Cl. .................. 435/7.1; 435/375; 544/247; 560/3

(58) Field of Classification Search ............... 530/300, 530/350; 536/23.1, 23.5; 435/4, 32.5, 375, 435/377
See application file for complete search history.

(56) References Cited

OTHER PUBLICATIONS

Djouhri et al. Sensory and electrophysiological properties of guinea-pig sensory neurones expressing Nav 1.7 (PN1) Na+ channel alpha subunit protein. J Physiol. 546(Pt 2):565-576, 2003.*
Rozhmanova OM et al. Neurophysiology 30(4-5): 250-252, 1999.*
Rozhmanova OM et al. Effect of Recombinant Interferon-2b (Laferon) on Transport of Sodium Ions in Human Neuroblastoma CellsNeurophysiology 33(1): 19-22, 2001.*
Chevrier et al. Differential modulation of Nav1.7 and Nav1.8 peripheral nerve sodium channels by the local anesthetic lidocaine. Brit J Pharmacol 142: 576-584, 2004.*
Nassar et al. Nociceptor-specific gene deletion reveals a major role for Nav1.7 (PN1) in acute and inflammatory pain. Proc Natl Acad Sci USA 101(34): 12706-12711, 2004.*
Urenjak et al. Neuroprotection-rationale for pharmacological modulation of Na+-channels. Amino Acids 14: 151-158, 1998.*
Akopian et al., "Structure and Distribution of a Broadly Expressed Atypical Sodium Channel", *Febs Letters* (1997) 400(2):183-187.
Akopian et al., "The Tetrodotoxin-Resistant Sodium Channel SNS has a Specialized Function in Pain Pathways", *Nature Neurosci.* (1999) 2(6):541-548.
Amir et al., "Membrane Potential Oscillations in Dorsal Root Ganglion Neurons: Role in Normal Electrogenesis and Neuropathic Pain", *J. Neurosci.* (1999) 19(19):8589-8596.
Black et al., "Up-regulation of a Silent Sodium Channel After Peripheral, But Not Central, Nerve Injury in DRG Neurons", *J. Neurophysiol.* (1999) 82(5):2776-2785.

Black et al., "Spinal Sensory Neurons Express Multiple Sodium Channel: α-Subunit mRNAs", *Mol. Brain Res.* (1996) 43(1/2):117-131.
Black et al., "NGF has Opposing Effects on Na+ Channel III and SNS Gene Expression in Spinal Sensory Neurons", *NeuroReport* (1997) 8(9-10):2331-2335.
Boucher et al., "Potent Analgesic Effects of GDNF in Neuropathic Pain States", *Science* (Washington, D. C.) (2000) 290(5489):124-127.
Chabal et al., "The Effect of Intravenous Lidocaine, Tocainide, and Mexiletine on Spontaneously Active Fibers Originating in Rat Sciatic Neuromas", *Pain* (1989) 38(3):333-338.
Chahine et al., "Electrophysiological Characteristics of Cloned Skeletal and Cardiac Muscle Sodium Channels", *Am. J. Physiol.* (1996) 271(2, Pt. 2):H498-506.
Chaplan et al., "Sodium Channel Type III is Up-Regulated in Three Mechanistically Different Models of Experimental Allodynia", *J. Pain* (2001) 2(2):S1: p. 21, Abstract #758.
Chen et al., "Cloning, Distribution and Functional Analysis of the Type III Sodium Channel from Human Brain", *Eur. J. Neurosci.* (2000) 12(12):4281-4289.
Clare et al., "Voltage-Gated Sodium Channels as Therapeutic Targets", *Drug Discovery Today* (2000) 5(11):506-520.
Coward et al., "Plasticity of TTX-Sensitive Sodium Channels PN1 and Brain III in Injured Human Nerves", *NeuroReport* (2001) 12(3):495-500.
Coward et al., "Sodium Channel β1 and β2 Subunits Parallel SNS/PN3 α-Subunit Changes in Injured Human Sensory Neurons", *NeuroReport* (2001) 12(3):483-488.
Cummins et al., "Nav1.3 Sodium Channels: Rapid Re-Priming and Slow Closed-State Inactivation Display Quantitative Differences After Expression in a Mammalian Cell Line and in Spinal Sensory Neurons", *J. Neurosci.* (2001) 21(16):5952-5961.
Cummins et al., "Slow Closed-State Inactivation: A Novel Mechanism Underlying Ramp Currents in Cells Expressing the hNE/PN1 Sodium Channel", *J. Neurosci.* (1998) 18(23):9607-9619.
T. R. Cummins and S. G. Waxman, "Down-regulation of Tetrodotoxin-Resistant Sodium Currents and Up-regulation of a Rapidly Re-priming Tetrodotoxin-Sensitive Sodium Current in Small Spinal Sensory Neurons After Nerve Injury", *J. Neurosci.* (1997) 17(10):3503-3514.
Devor et al., "Systemic Lidocaine Silences Ectopic Neuroma and DRG Discharge Without Blocking Nerve Conduction", *Pain* (1992) 48(2):261-268.
Dib-Hajj et al., "Plasticity of Sodium Channel Expression in DRG Neurons in the Chronic Constriction Injury Model of Neuropathic Pain", *Pain* (1999) 83(3):591-600.
Diss et al., "Expression Profiles of Voltage-Gated Na(+) Channel Alpha-Subunit Genes in Rat and Human Prostate Cancer Cell Lines", *Prostate* (2001) 48(3):165-178.

(Continued)

*Primary Examiner*—Bridget Bunner
(74) *Attorney, Agent, or Firm*—Woodcock Washburn LLP

(57) ABSTRACT

The present invention provides methods to manipulate differentiation of a neuroblastoma cell line (IMR-32) such that predominant $Na_v$ expression is either $Na_v1.3$ in IMR-32 cells exposed to retinoic acid or $Na_v1.7$ in cells grown under non-differentiating conditions. The cells of the present invention are useful for the discovery of new compounds that modulate the function of either $Na_v1.3$ and/or $Na_v1.7$.

3 Claims, 16 Drawing Sheets

OTHER PUBLICATIONS

Doyle et al., "The Structure of the Potassium Channel: Molecular Basis of K+ Conduction and Selectivity", *Science* (Washington, D.C.) (1998) 280(5360):69-77.

Dubin et al., "Lysophosphatidic Acid Stimulates Neurotransmitter-Like Conductance Changes that Precede GABA and L-Glutamate in Early, Presumptive Cortical Neuroblasts", *J. Neurosci.* (1999) 19(4):1371-1381.

England et al., "Inflammation Induces Increased Expression of the PN1 Sodium Channel in Sensory Neurons", Peripheral Nerve Society, La Jolla, California (Jul. 21-25, 1999), Slide Presentation Abstract, p. 44.

Harry A. Fozzard and Dorothy A. Hanck, "Structure and Function of Voltage-Dependent Sodium Channels: Comparison of Brain II and Cardiac Isoforms", *Physiol. Rev.* (1996) 76(3):887-926.

Goldin et al., "Nomenclature of Voltage-Gated Sodium Channels", *Neuron* (2000) 28(2):365-368.

S. Gurtu and P. A. Smith, "Electrophysiological Characteristics of Hamster Dorsal Root Ganglion Cells and Their Response to Axotomy", *J. Neurophysiol.* (1988) 59(2):408-423.

Hamill et al., "Improved Patch-Clamp Techniques for High-Resolution Current Recording from Cells and Cell-Free Membrane Patches", *Pflugers Archiv. Eur. J. Physiol.* (1981) 391(2):85-100.

Lori L. Isom, "Pathobiology of Visceral Pain: Molecular Mechanisms and Therapeutic Implications I: Cellular and Molecular Biology of Sodium Channel .Beta.-subunits—Therapeutic Implications for Pain?", *Am. J. Physiol.* (2000) 278(3, Pt. 1):G349-353.

Lori L. Isom, "Sodium Channel β-Subunits: Anything But Auxiliary", *Neuroscientist* (2001) 7(1):42-54.

S. H. Kim and J. M. Chung, "An Experimental Model for Peripheral Neuropathy Produced by Segmental Spinal Nerve Ligation in the Rat", *Pain* (1992) 50(3):355-363.

Orna Matzner and Marshall Devor, "Hyperexcitability at Sites of Nerve Injury Depends on Voltage-Sensitive Na+ Channels", *J. Neurophys.* (1994) 72(1):349-359.

Oh et al., "Na+ Channel β1 Subunit mRNA: Differential Expression in Rat Spinal Sensory Neurons", *Mol. Brain Res.* (1995) 30(2):357-361.

N. W. Plummer and M. H. Meisler, "Evolution and Diversity of Mammalian Sodium Channel Genes", *Genomics* (1999) 57(2):323-331.

Sangameswaran et al., "A Novel Tetrodotoxin-Sensitive, Voltage-Gated Sodium Channel Expressed in Rat and Human Dorsal Root Ganglia", *J. Biol. Chem.* (1997) 272(23):14805-14809.

Shah et al., "β3: A Novel Auxiliary Subunit for the Voltage Gated Sodium Channel is Up-Regulated in Sensory Neurones Following Streptozocin-Induced Diabetic Neuropathy in Rat", *Neurosci. Lett.* (2001) 309(1):1-4.

Sotgiu et al., "Effect of Systemic Lidocaine on Dorsal Horn Neuron Hyperactivity Following Chronic Peripheral Nerve Injury in Rats", *Somatosensory and Motor Research* (1992) 9(3):227-233.

Darrell L. Tanelian and M. Bruce MacIver, "Analgesic Concentrations of Lidocaine Suppress Tonic A-Delta and C Fiber Discharges Produced by Acute Injury", *Anesthesiology* (1991) 74(5):934-936.

Toledo Aral et al., "Identification of PN1, a Predominant Voltage-Dependent Sodium Channel Expressed Principally in Peripheral Neurons", *P.N.A.S., U.S.A.* (1997) 94(4):1527-1532.

Tumilowicz et al., "Definition of a Continuous Human Cell Line Derived from Neuroblastoma", *Cancer Res.* (1970) 30:2110-2118.

S. G. Waxman, "The Molecular Pathophysiology of Pain: Abnormal Expression of Sodium Channel Genes and its Contributions to Hyperexcitability of Primary Sensory Neurons", *Pain* (1999) 82(Supp. 6):S133-S140.

Waxman et al., "Type III Sodium Channel mRNA is Expressed in Embryonic But Not Adult Spinal Sensory Neurons, and is Re-Expressed Following Axotomy", *J. Neurophysiol.* (1994) 72(1):466-470.

Whitaker et al., "Changes in the mRNAs Encoding Voltage-Gated Sodium Channel Types II and III in Human Epileptic Hippocampus", *Neuroscience* (Oxford, U.K.) (2001) 106(2):275-285.

Shah, B. S. et al., "Developmental expression of the novel voltage-gated sodium channel auxiliary subunit β3, in rat CNS," *J Physiol* (2001), 534(3):763-776.

Safo, P. et al., "Distinction among Neuronal Subtypes of Voltage-Activated Sodium Channels by μ-Conotoxin PIIIA," *Journal of Neuroscience*, Jan. 1, 2000, 20(1), 76-80.

Choi, D-Y. et al., "Sustained Signaling by Phospholipase C-γ Mediates Nerve Growth Factor-Triggered Gene Expression," *Molecular and Cellular Biology*, Apr. 2001, 21(8), 2695-2705.

Kucher, V. V. et al., "Modulation of Voltage-Gated Sodium Channels by Recombinant Interferon—α2b in Human Neuroblastoma Cells IMR-32," *Ukrainian Biochemical Journal*, 2001, 73(3), 112-115 [English summary on p. 115].

\* cited by examiner

SCN mRNA Expression

Panel A

Panel B

Panel A

Panel B

Panel C

Panel A

Panel B

Panel A

Panel B

Panel A

Panel B

Panel C

Panel D

Panel A

Panel B

Panel C

Panel D

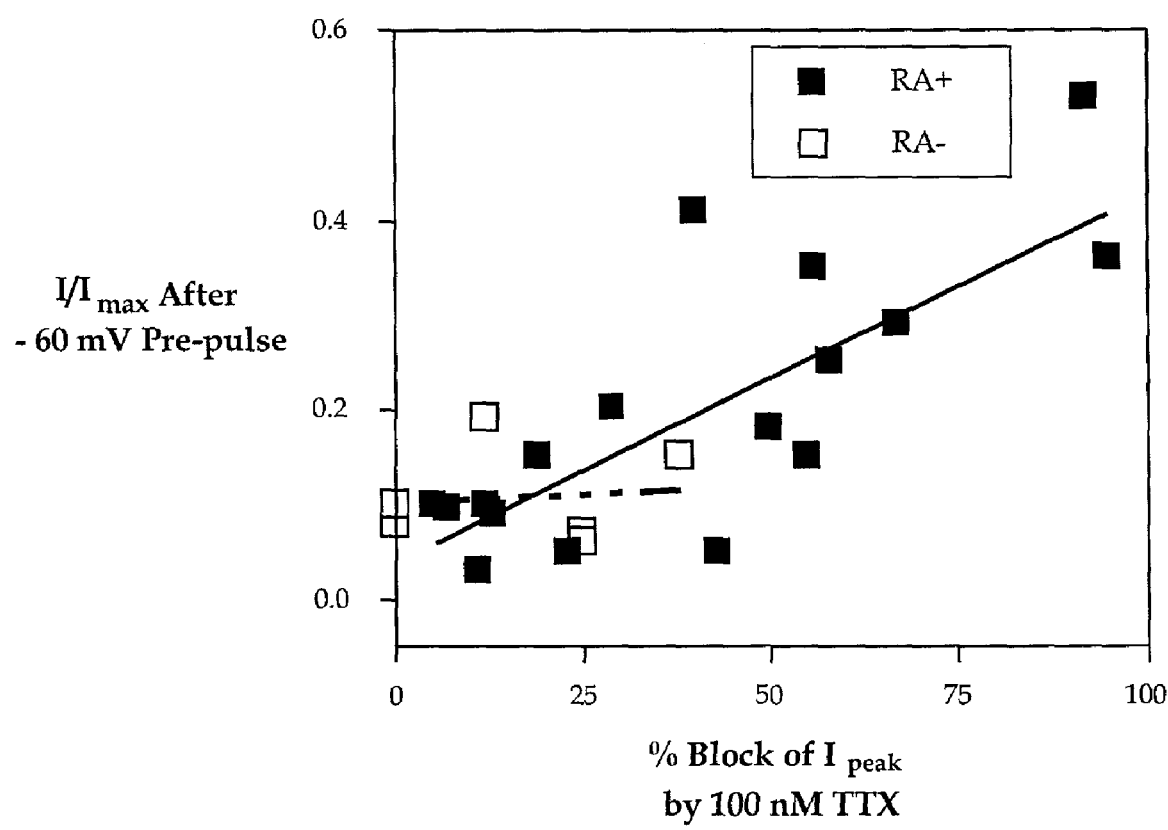

Panel B

Panel C

METHOD FOR IDENTIFYING MODULATORS OF NA$_V$ ION CHANNELS

BACKGROUND OF INVENTION

Voltage-gated sodium (Na) channels (Na$_v$) are complex integral membrane proteins that open by depolarization, allowing the influx of Na$^+$ions which, in turn, mediate the fast depolarization phase of an action potential in many excitable cells, e.g., neurons, neuroendocrine cells, and cardiac and skeletal myocytes. The nine known alpha pore-forming Na$_v$ subunits that have been functionally expressed are classified into two major pharmacological groups: Na$_v$ that are either i) sensitive or ii) insensitive to tetrodotoxin (TTX), a lethal toxin isolated from puffer fish (Fugu. sp). TTX-sensitive (TTX-S) channels are blocked by low nM concentrations of TTX while TTX-resistant (TTX-R) channels are blocked by μM concentrations of TTX. Members of the TTX-S class include SCN1a (Na$_v$1.1), SCN2a (Na$_v$ 1.2), SCN3a (Na$_v$1.3), SCN4a (Na$_v$1.4), SCN8a (Na$_v$1.6), and SCN9a (Nav1.7). Members of the TTX-R class include SCN5a (Na$_v$1.5), SCN10a (Na$_v$1.8), SCN12a (Na$_v$1.9) (Clare et al. (2000); Goldin et al. (2000)). SCN6a/SCN7a has not been functionally expressed; however, it is predicted to be TTX-sensitive since it contains an aromatic amino acid (Y) in the pore region of domain I known to be required for TTX blockade (Akopian et al. (1997)). Na$_v$ alpha subunits are very large and share features with calcium channels and the prototype K$_v$ potassium channels first described in *Drosophila* (Fozzard and Hanck (1996)). It is believed that channels in this large super-family are formed by the association of four similar domains, each with six putative transmembrane segments (S1–6) and a pore (P) domain. In the case of the classical Na and Ca channels, these four domains are combined in a single gene: Domains I–IV (Plummer and Meisler (1999)). Na$_v$ alpha subunits form complexes with one or two beta subunits, probably through covalent interactions (Isom (2000); Isom (2001)). A variety of toxins have been shown to bind to other sites on Na$_v$ channels, including site-2 toxins that bind to site-2 and lead to persistent activation (e.g. veratridine and batrachotoxin). Local anesthetics interact with amino acids in the S6 transmembrane region of domain IV, which, by analogy to the crystallized K channel KcsA (Doyle et al. (1998)), are thought to line the pore (Clare et al. (2000)).

From a therapeutic perspective, pharmacological and kinetic differences of Na$_v$ isoforms provide a basis for developing tissue-specific therapeutic agents. For example, some local anesthetic agents (e.g. lidocaine) have a greater efficacy in the heart than in the nervous system, while guanidinium and μ-CTX toxins discriminate between heart, skeletal and nerve Na channels (Fozzard and Hanck, (1996)). Other antagonists have been found to block Na channel activity in a use-dependent manner by binding to specific channel conformations presented in closed, activated or inactivated states. These use-dependent blockers target aberrantly hyperactive channels in certain human diseases and thus, can be utilized to assist rational therapeutic development. However, these are rare examples of Na$_v$ subtype-specific antagonists. Fortunately, molecular identification and pharmacological characterization of channels underlying endogenous Na currents in cells may enable the association of specific Na$_v$ subtypes to specific diseases. Aberrant Na$_v$ expression has been identified as a contributing factor to human disease and debilitation including epilepsy, long QT syndrome, and paralysis. Recent investigation has implicated aberrant Na$_v$ expression as contributing to neuropathic pain (reviewed by Clare et al., 2000). For example, examination of injured DRG neurons reveals enhanced expression of certain Na$_v$ channels including the TTX-sensitive Na$_v$ alpha subunit SCN3a. Following nerve injury, neurons of the Dorsal Root Ganglion (DRG) become spontaneously active, activate at lower thermal and mechanical stimuli intensities and fire repetitively to suprathreshold stimuli (Gurtu and Smith (1988)). The elevated spontaneous activity in injured DRG can be blocked by local anesthetics (Chabal et al. (1989); Tanelian and MacIver (1991); Devor et al. (1992); Sotgiu et al. (1992); and Matzner and Devor (1994)), a class of compounds known to target Na$_v$, as well as TTX (Amir et al. (1999)). In addition, it has been observed that peripheral axotomy of sensory neurons leads to an increase in a TTX-S sodium current with a SCN3a-like kinetics, having a significantly faster recovery from inactivation (τ~15 msec) compared to TTX-S sodium currents in control rat neurons (τ~60 msec) (Cummins and Waxman (1997)). Noteworthy, in some skeletal muscle Na$_v$ channelopathies, including paramyotonia congenita, an increased rate of Na$_v$ recovery from inactivation appears to contribute to the hyperexcitability of skeletal muscle by reducing the refractory period (Chahine et al. (1996)).

Delayed hyperexcitability that develops following peripheral nerve injury (thought to underlie some types of "neuropathic pain") correlates with novel Na$_v$ expression including up-regulation of the TTX-sensitive alpha subunit Na$_v$1.3 (SCN3a) in both unmyelinated and myelinated sensory neurons (Waxman (1999)). Numerous studies have demonstrated that peripheral nerve injury increases Na$_v$1.3 expression in rat DRG neurons (Waxman et al. (1994); Black et al. (1999); Dib-Hajj et al. (1999)). For example, intrathecal application of GDNF reversed the upregulation of Nav1.3 after spinal nerve ligation (method: Kim and Chung, 1992) and attenuated aberrant ectopic activity and neuropathic pain behavior (Boucher et al. (2000)). Relatedly, in cultured dissociated small nociceptive DRG neurons, addition of Nerve Growth Factor (NGF) results in down-regulation of SCN3a mRNA (Black et al. (1997)). SCN3a is believed to contribute to neuronal hyperexcitability as a result of its ability to rapidly "reprime" (recovery from inactivation) during the re-polarization phase of the action potential. For example, in small rat DRG neurons, increased expression of Na$_v$1.3 after peripheral axotomy correlated with a switch from a TTX-S current with slow recovery from inactivation to a TTX-S current with a four-fold more rapid recovery (rapid re-priming), resulting in increased frequency of repetitive firing (Cummins and Waxman (1997)). Physiological properties (e.g. development of and recovery from inactivation) of the up-regulated Na channel in axotomized DRG are nearly identical to SCN3a when compared to SCN3a transiently expressed in certain cell types (Cummins et al. (2001)). Black and colleagues showed increased SCN3a immunoreactivity in adult rat small DRG neurons after axotomy of peripheral sciatic nerve processes but not dorsal rhizotomy (Black et al. (1999)). Furthermore, expression of a rapidly-re-priming Na current was restricted to peripherally, not centrally, axotomized small DRG neurons (Black et al. (1999)). Similarly, Chaplan and colleagues demonstrated by quantitative PCR up-regulation of Na$_v$1.3 mRNA in lumbar sensory spinal ganglia isolated from diabetic rats and rats treated with the chemotoxic agent vincristine (Chaplan, Calcutt and Higuera, *Journal of Pain* (2001) 2(2):S1:21). Aberrant SCN3a expression following peripheral nerve injury also occurs in humans. Coward and colleagues demonstrated SCN3a (Na$_v$1.3) immunoreactivity in a subset of peripheral nerve fibers from patients that had experienced peripheral or central nerve injury. Consistent with data obtained in rat neuropathic pain models, no detectable increase in soma labeling was observed after central avulsion (axotomy) in humans (Coward et al. (2001)). Whether SCN3a is up-regulated in human DRG neurons after peripheral axotomy requires further investigation.

When compared, the kinetic and pharmacologic properties of human (Chen et al. (2000)) and rat (Cummins et al. (2001)) recombinant SCN3a channels are similar. For example, the recovery from inactivation time constant is ~20 msec when membrane potential is held at −90 mV for both human and rat receptors (compare FIGS. 4 and 5 of Chen et al. (2000) with FIG. 4 of Cummins et al. (2001)). The voltage dependence of activation and inactivation are similar as well (midpoints of activation were −23 and −25 mV for human and rat, respectively; half steady state inactivation potentials were −69 and −65 mV, respectively). The similarity of rat and human SCN3a functional properties supports the hypothesis that increased expression of SCN3a in injured human DRG will likely contribute to enhanced firing frequencies similar to those observed in injured rat DRG neurons. The beta subunit(s) associated with the up-regulated SCN3a channel in injured DRG neurons are unknown. At least two Na channel beta subunits (β1 and β3) are known to be expressed in DRG neurons (Oh et al. (1995); Coward et al. (2001); Shah et al. (2001)), and it has been reported that in the CCI model of neuropathic pain there is 20% up-regulation of β3 in small diameter DRG neurons (Shah et al. (2001)). Co-expression of β1, β2, β1+β2, or β3 with $Na_v1.3$ revealed that $Na_v1.3$ voltage dependence of activation was shifted +7 mV in the presence of only β3. Furthermore, β3 shifted the voltage dependence of inactivation to the right by +7 mV, and β1+β2 (but neither alone) shifted it by +5 mV (Cummins et al. (2001)). To date, β2 has not been detected in cultured rat DRG neurons (Black et al. (1996)). Examined collectively, the aforementioned study data provide strong evidence that over-expression of Nav 1.3 in injured DRG neurons contributes to the genesis and maintenance of neuropathic pain in animals, including humans.

Interestingly, PN1 (also known as SCN9a, hNE (NeuroEndocrine channel) and $Na_v1.7$) is another TTX-sensitive $Na_v$ alpha subunit preferentially-expressed in rat and human injured DRG neurons, trigeminal ganglion neurons and sympathetic neurons (Toledo Aral et al. (1997)). PN1 has been reported to be up-regulated in small diameter sensory neurons up to three months following CFA-induced inflammation of peripheral receptive fields [England et al., Peripheral Nerve Society Abstract (1999)]. In SNS null mice, a 50% up-regulation of PN1 mRNA was suggested to compensate for the hypoalgesia caused by the absence of SNS in carrageenan-induced inflammation [Akopain et al., *Nat. Neurosci,* (1999) 2:541]. Examination of injured human DRGs reveals that regulation of PN1 is similar to that of TTX-R channels (Coward et al. (2001)). Furthermore, RT-PCR data suggest a positive correlation between up-regulation of $Na_v1.7$ (and $Na_v1.3$) and the metastatic potential of prostate tumor cell lines (Diss et al. (2001)). Therefore, inhibitors of $Na_v1.7$ and $Na_v1.3$ may have therapeutic potential in curbing metastasis in certain cancers including prostate cancer.

Unfortunately, conventional therapy for treating neuropathic pain in humans due to ectopic (spontaneous) $Na_v$ activity, including administration of analgesics, anticonvulsants and anti-arrhythmics, has proven sporadically effective with demonstrable side-effects as a consequence of non-specific, low-potency interactions at $Na_v$ targets. This fact, coupled with a growing population of neuropathic pain sufferers, reveals the importance and immediate need for $Na_v$ subtype-specific antagonists. Historically, however, it has been the difficulty in constructing cell lines that stably express $Na_v$ subtypes that has slowed target-driven therapeutic design (Clare et al. (2000)).

SUMMARY OF INVENTION

Sodium channel alpha subunit expression was regulated in IMR-32 cells by retinoic acid (RA). Quantitative PCR examination of IMR-32 cells exposed to RA revealed up-regulation of endogenously expressed $Na_v1.3$ mRNA and down-regulation of other TTX-sensitive (TTX-S) $Na_v$, including $Na_v1.7$ (FIG. 1). Western analysis indicated that Nav1.3 protein was expressed in IMR-32 cells maintained in RA (FIG. 3A). Thus, IMR-32 cells maintained in RA were ideally suited to screen for modulators of $Na_v1.3$ activity in cell-based assays including veratridine-induced depolarization as measured by a voltage sensitive dye (FIG. 4). Quantitative PCR examination of IMR-32 cells cultured without RA revealed significant up-regulation of $Na_v1.7$ (SCN9a) mRNA (FIG. 1A). Western analysis indicated that Nav1.7 protein was expressed in IMR-32 cells cultured without supplements (FIG. 3B). Accordingly, these cells are ideally suited to screen for modulators of $Na_v1.7$ activity in cell-based assays. The electrophysiological characteristics of fast transient TTX-sensitive sodium currents expressed in cells with RA were consistent with the expression of SCN3a $Na_v$ (FIGS. 5 to 7 and 9). Inward currents in cells grown without RA were consistent with the expression of $Na_v1.7Na_v$ channels (FIG. 8). $Na_v1.3$ and $Na_v1.7$-specific antagonists are useful as therapeutic agents in treating human pathologies mediated (at least in part) by aberrant $Na_v1.3$ and $Na_v1.7$ expression. Manipulation of endogenous $Na_v$ expression in IMR-32 cells by RA treatment in order to identify $Na_v$ antagonists is a novel methodology that incorporates the following procedures:

1) Undifferentiated IMR-32 cells were induced to differentiate by adding 9-cis RA (1 μM final) to normal IMR-32 growth medium, resulting in up-regulation of endogenous $Na_v1.3$ expression and down-regulation of other TTX-S $Na_v$, while culturing IMR-32 cells without RA was employed to maintain predominant expression of $Na_v1.7$.
2) Temporal changes in endogenous TTX-S $Na_v$ expression were assessed by quantitative PCR of cDNA templates synthesized from total RNA of undifferentiated and RA-induced differentiated IMR-32 cells.
3) RA-induced differentiated IMR-32 cells that predominantly expressed $Na_v1.3$ were used to identify $Na_v1.3$ channel antagonists in a cell-based assay.
4) IMR-32 cells cultured without RA that predominantly expressed $Na_v1.7$ were used to identify $Na_v1.7$ channel antagonists in a cell-based assay.

Panel A: IMR-32 cells maintained in media supplemented with 1 μM retinoic acid. Specific detection of human $Na_v1.3$ protein isoforms by rabbit anti-rat $Na_v1.3$ antibody ($Na_v1.3$ Ig). Lane 1: $Na_v1.3$ Ig (1:300) recognized human $Na_v1.3$ protein isoforms of 215 kd, 160 kd, 135 kd and 115 kd. Lane 2: Pre-incubation of $Na_v1.3$ Ig (1:300) with rat $Na_v1.3$ peptide (1:1; mg:mg) blocked $Na_v1.3$ Ig recognition of human $Na_v1.3$ protein isoforms of 215 kd, 160 kd, 135 kd and 115 kd. Lane 3: Pre-incubation of $Na_v1.3$ Ig (1:300) with rat $Na_v$ Pan peptide (1:1; mg:mg) did not block $Na_v1.3$ Ig recognition of human $Na_v1.3$ protein isoforms of 215 kd, 160 kd, 135 kd and 115 kd.

Panel B: IMR-32 cells maintained in media supplemented without retinoic acid. Specific detection of human $Na_v1.7$ protein isoforms by rabbit anti-rat PN1 antiboby ($Na_v1.7$ Ig). Lane 1: $Na_v1.7$ Ig (1:300) recognized human $Na_v1.7$ protein isoforms of 225 kd and 97 kd. Lane 2: Pre-incubation of $Na_v1.7$ Ig (1:300) with rat $Na_v1.7$ peptide (1:1; mg:mg) blocked $Na_v1.7$ Ig recognition of human $Na_v1.7$ protein isoforms of 225 kd and 97 kd. Lane 3: Pre-incubation of $Na_v1.7$ Ig (1:300) with rat $Na_v$ Pan peptide (1:1; mg:mg) did not block $Na_v1.7$ Ig recognition of human $Na_v1.7$ protein isoforms of 225 kd and 97 kd.

Figure 4:
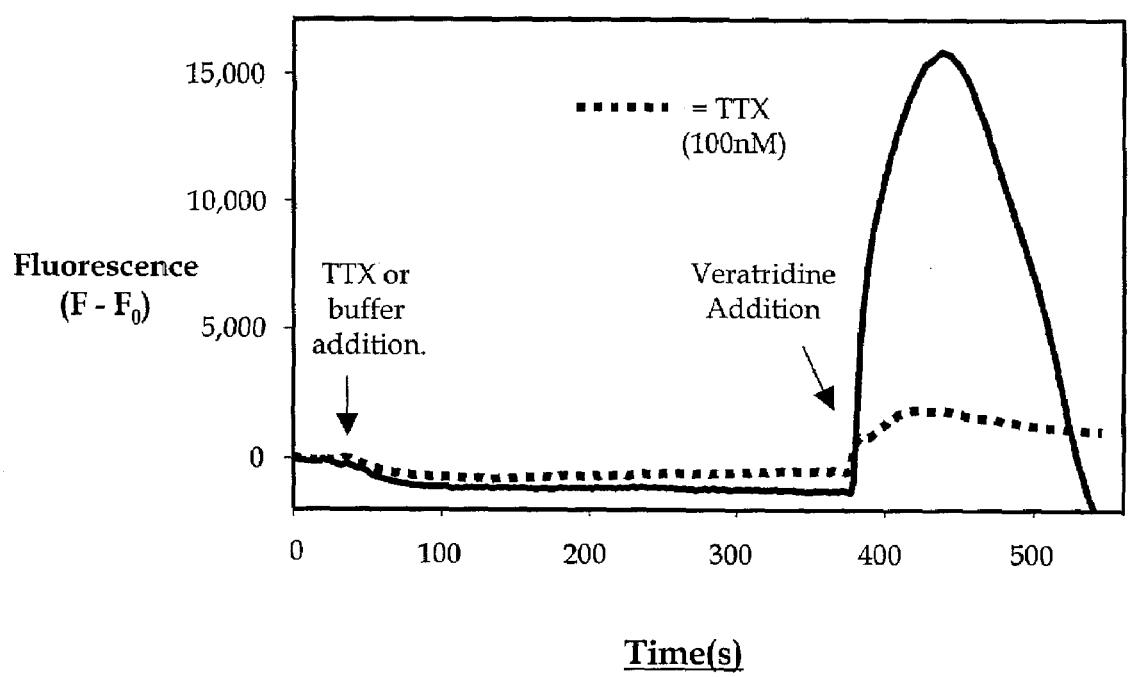
Figure 4:
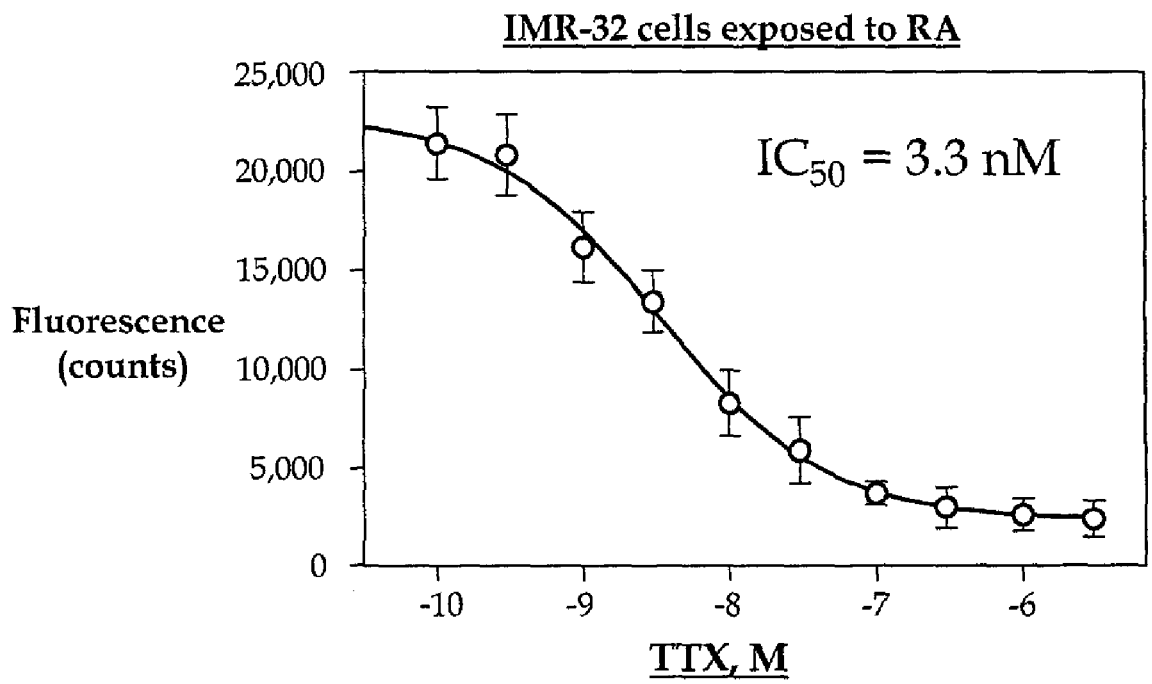
Figure 4:
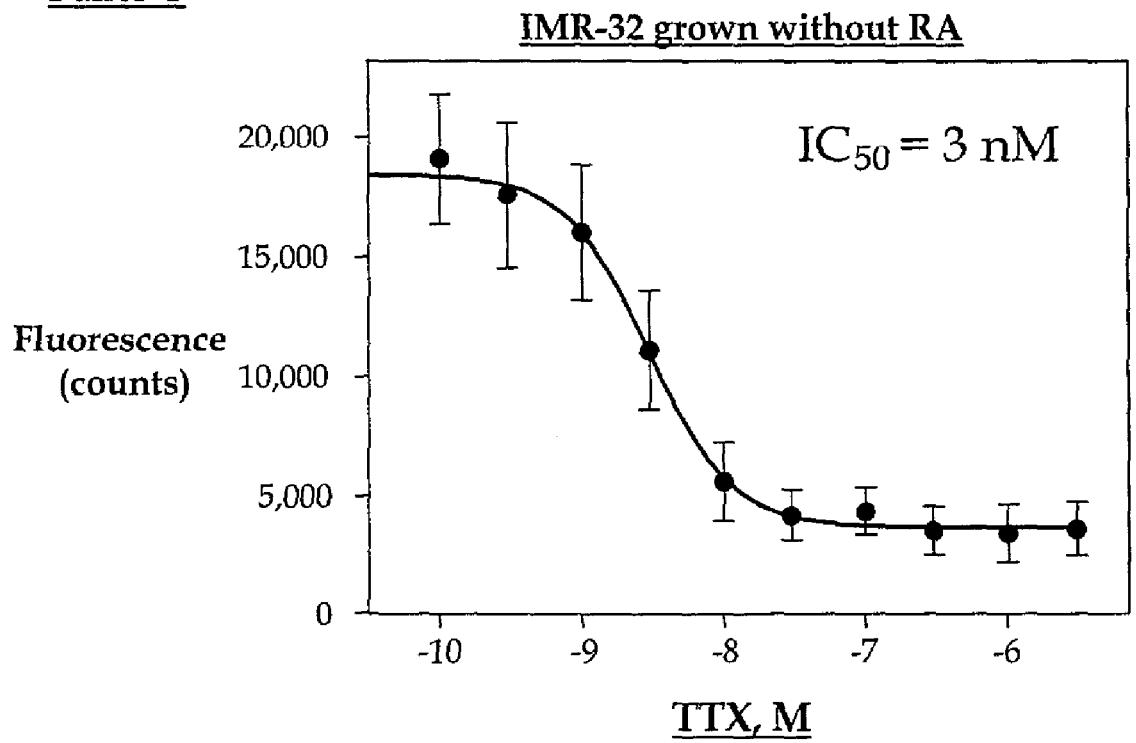

FIG. 4, Panels A, B and C: Veratridine-induced depolarization of IMR-32 cells maintained in the presence or absence of retinoic acid is blocked by tetrodotoxin (TTX) in a dose dependent manner using a voltage-sensitive dye-based fluorometric assay (FLIPR™).

Panel A: The depolarization induced by veratridine stimulated Na influx through Na channels in IMR-32 cells maintained in retinoic acid is shown as an increase in Fluorescence (F–F₀). TTX (100 nM; dotted line) or vehicle (solid line) was added on line at the first arrow and six minutes later veratridine (10 μM final concentration) was added to stimulate Na influx through $Na_v$ channels.

Panel B: TTX blocked veratridine-stimulated sodium influx in a dose dependent manner in IMR-32 cells grown in the presence of RA. Data from a representative experiment is shown ($IC_{50}$=3.3 nM).

Panel C: TTX blocked veratridine-stimulated sodium influx in a dose dependent manner in IMR-32 cells grown without RA. Data from a representative experiment is shown ($IC_{50}$=3.0 NM).

Figure 5:
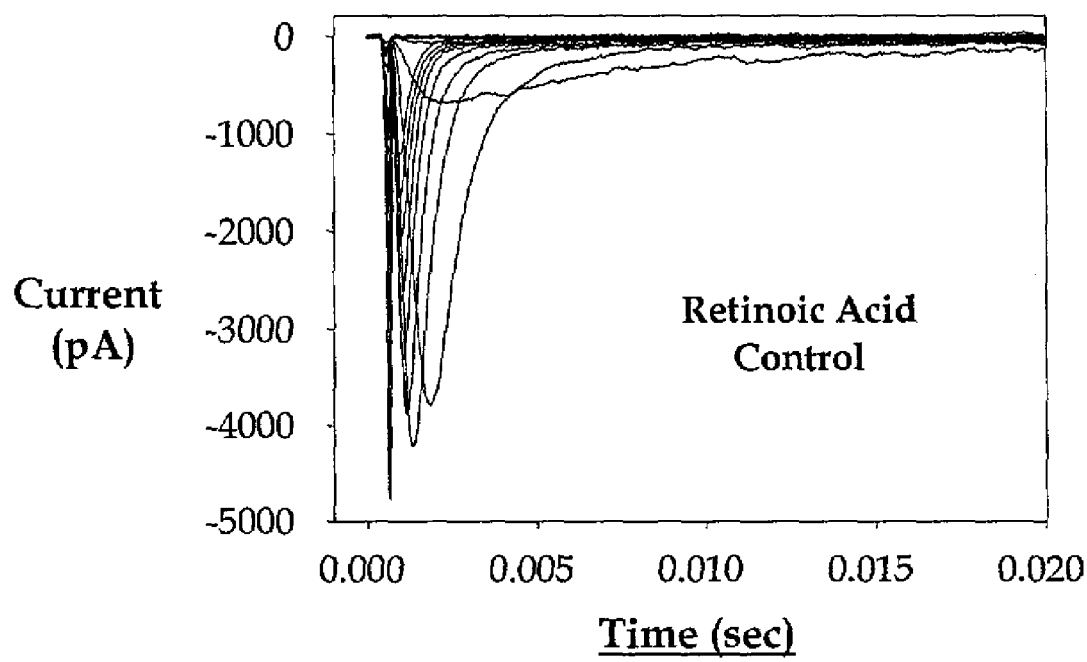
Figure 5:
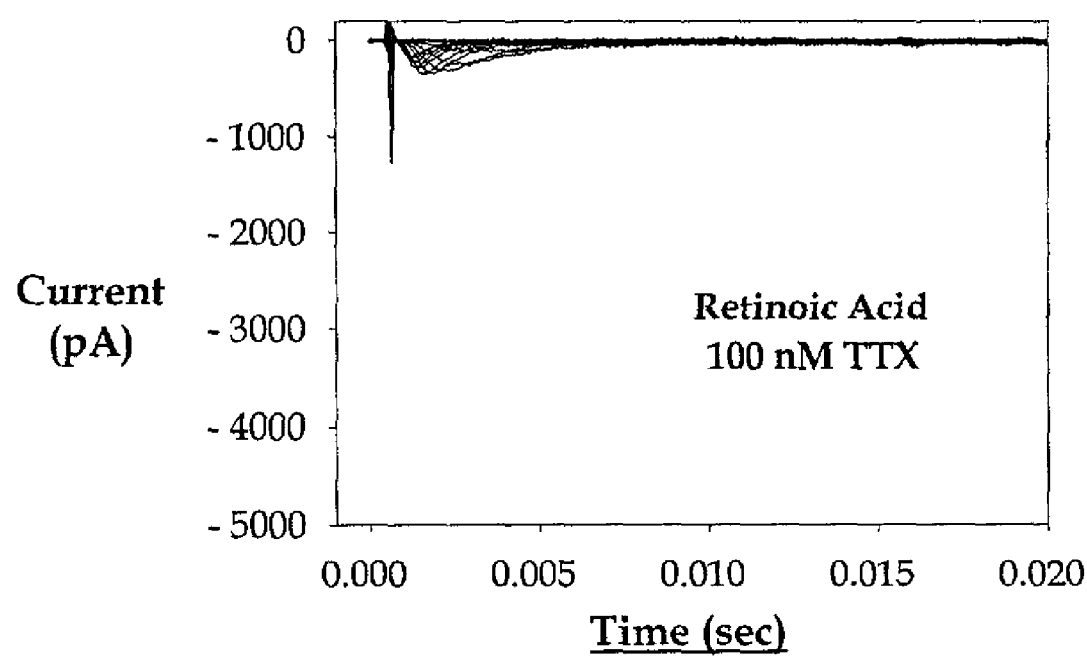
Figure 5:
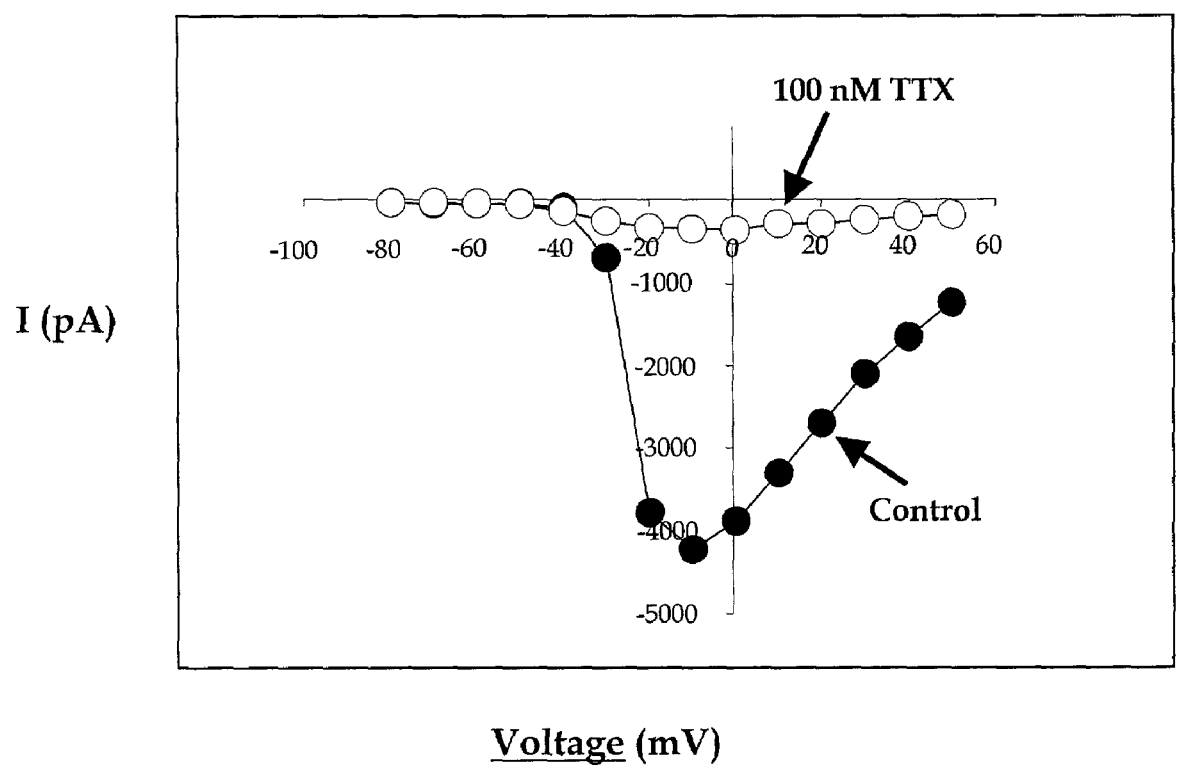

FIG. 5, Panels A and B: Tetrodotoxin (TTX; 100 nm) blocked fast transient inward currents in a population of IMR-32 cells grown in the presence of RA (1 μm).

Panel A: Voltage steps were applied between −80 and +50 mV in increments of 10 mV from a holding potential of −100 mV. In this cell, inward currents were nearly completely blocked by TTX (92%). The TTX blockade was reversible upon washout of toxin.

Panel B: Current-voltage curves for the families of currents shown in Panel A.

Figure 6:
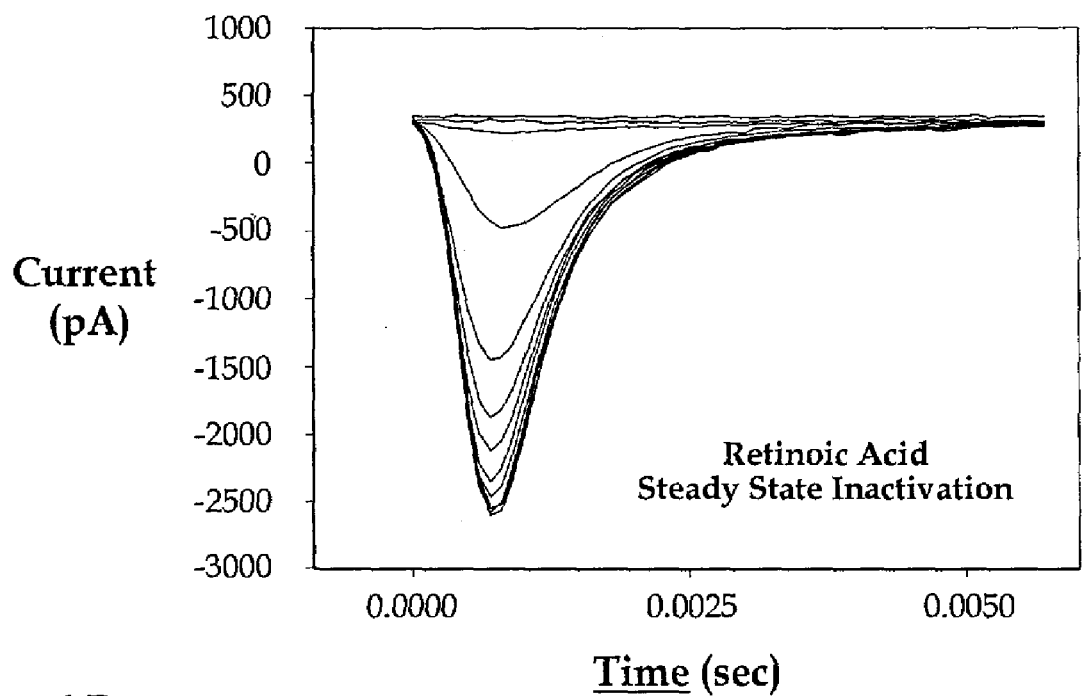
Figure 6:
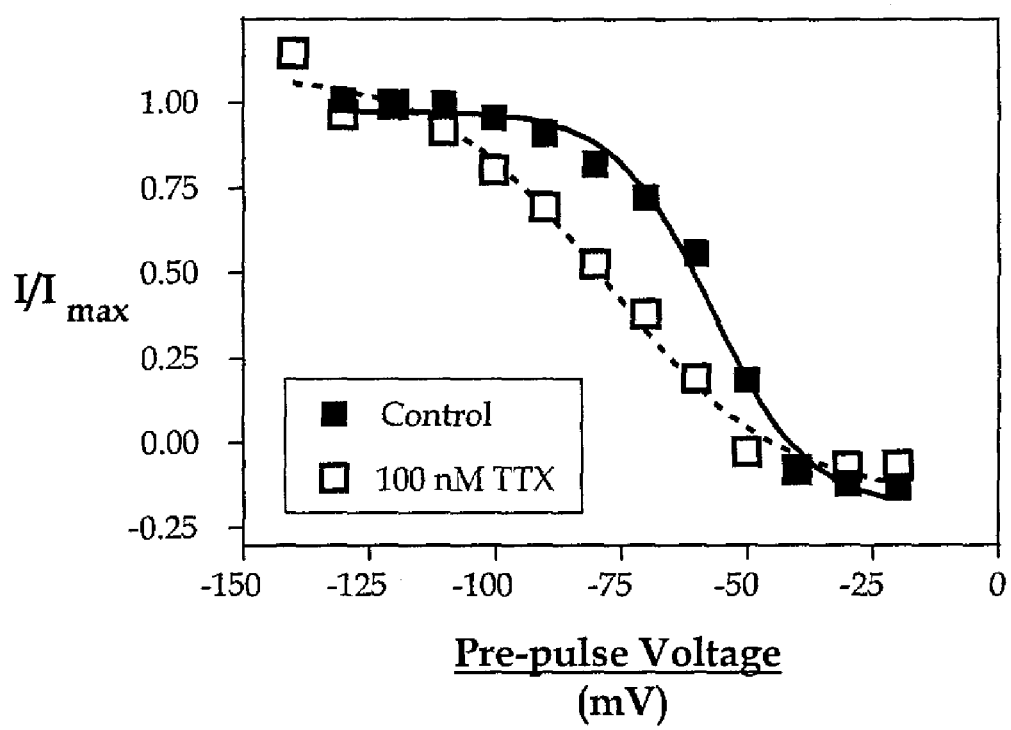

FIG. 6, Panels A and B: The voltage dependence of steady state inactivation shifts to the left in the presence of TTX (100 nM) in a population of IMR-32 cells grown in RA (1 μM).

Panel A: The membrane potential was held at −100 mV and subsequently stepped for 500 msec to pre-pulse potentials ranging between −140 and −20 mV in increments of 10 mV prior to a voltage step to 0 mV to elicit peak inward currents. TTX was not present.

Panel B: Plotted is the normalized peak current (I/Imax) obtained at 0 mV after the indicated pre-pulse potential. The maximum peak inward current was elicited after pre-pulse potentials more negative than −110 mV. Steady state inactivation curves are shown for a single cell in the absence (solid squares) and presence (clear squares) of TTX (100 nM). The TTX-S current had a $V_{0.5}$ more depolarized than the TTX-resistant components of the inward current. The TTX-R inward currents in these cells (RA+ as well as RA−) are largely composed of $Cd^{2+}$ and mibefradil-sensitive $Ca^{2+}$ currents.

Figure 7:
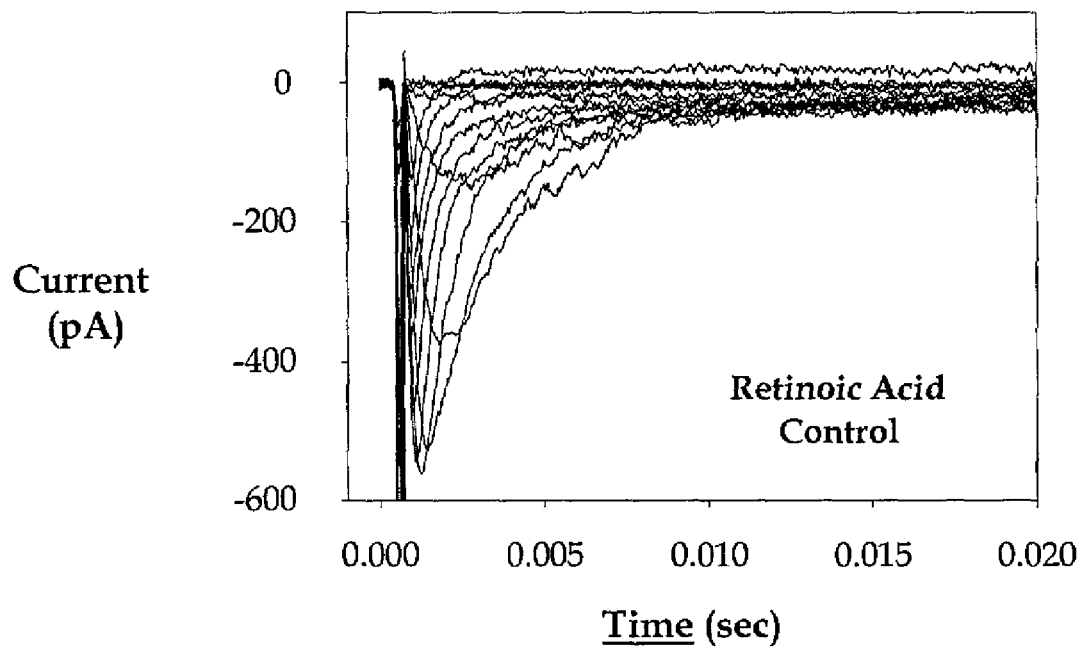
Figure 7:
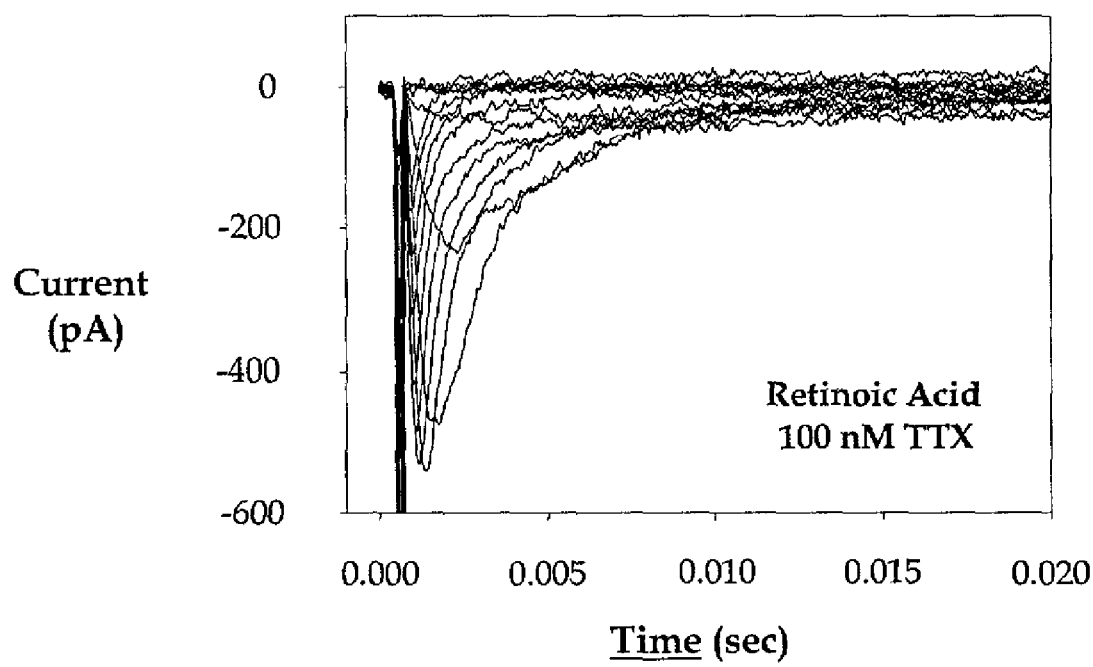
Figure 7:
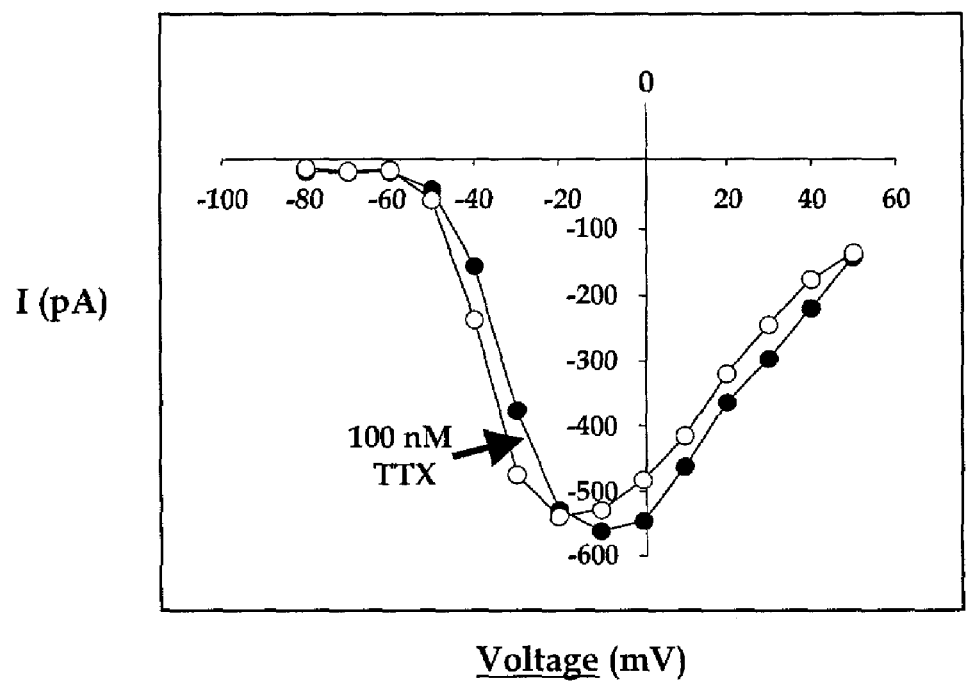
Figure 7:
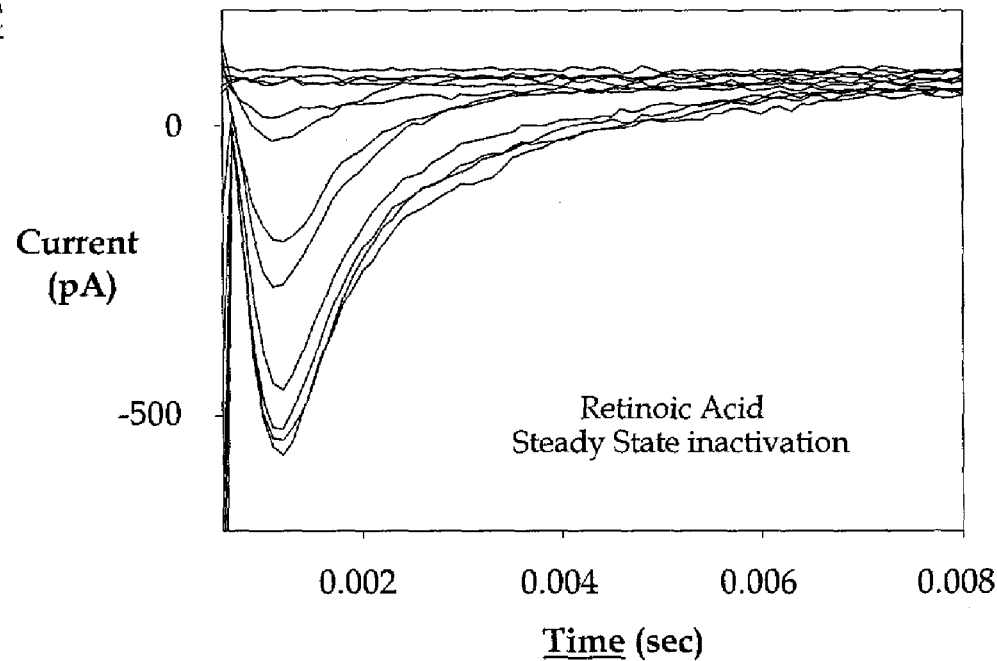
Figure 7:
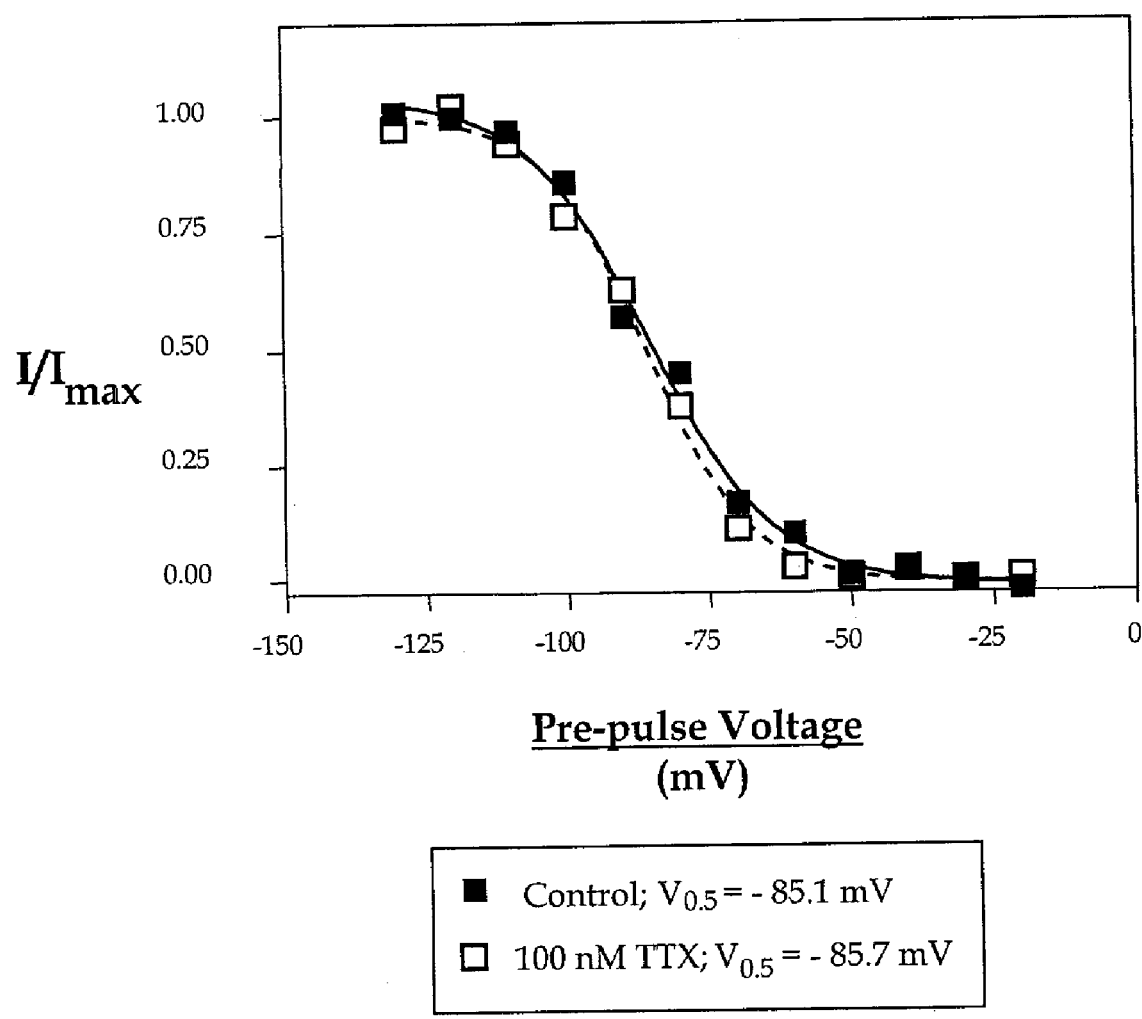

FIG. 7, Panels A, B, C and D: A second population of IMR-32 cells grown in RA was observed to have little or no TTX sensitivity (100 nM).

Panel A: Family of currents was elicited by voltage steps according to the protocol described in the previous figure.

Panel B: TTX (100 nM) had little effect on the inward currents elicited in this cell.

Panel C: Steady state inactivation in the absence of TTX was determined according to the protocol described in the legend for FIG. 6.

Panel D: The voltage dependence of steady state inactivation was not significantly altered in the presence of TTX (100 nM) and the $V_{0.5}$ was more negative than the TTX-S inward currents (−85 mV in this example).

Figure 8:
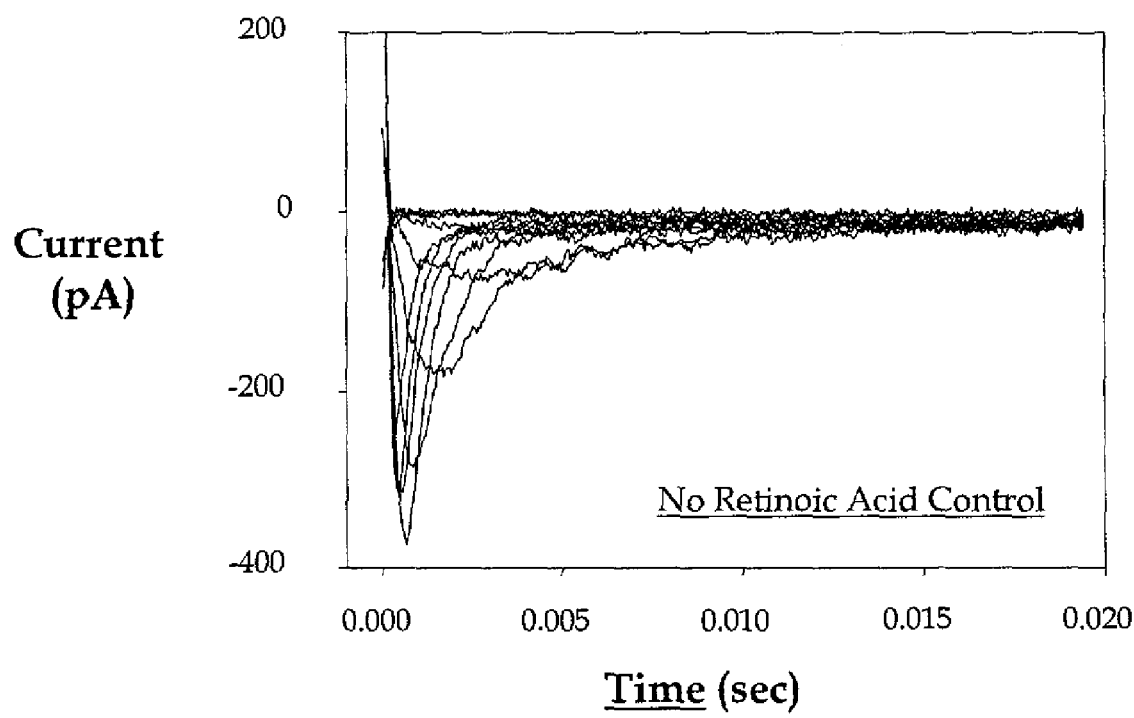
Figure 8:
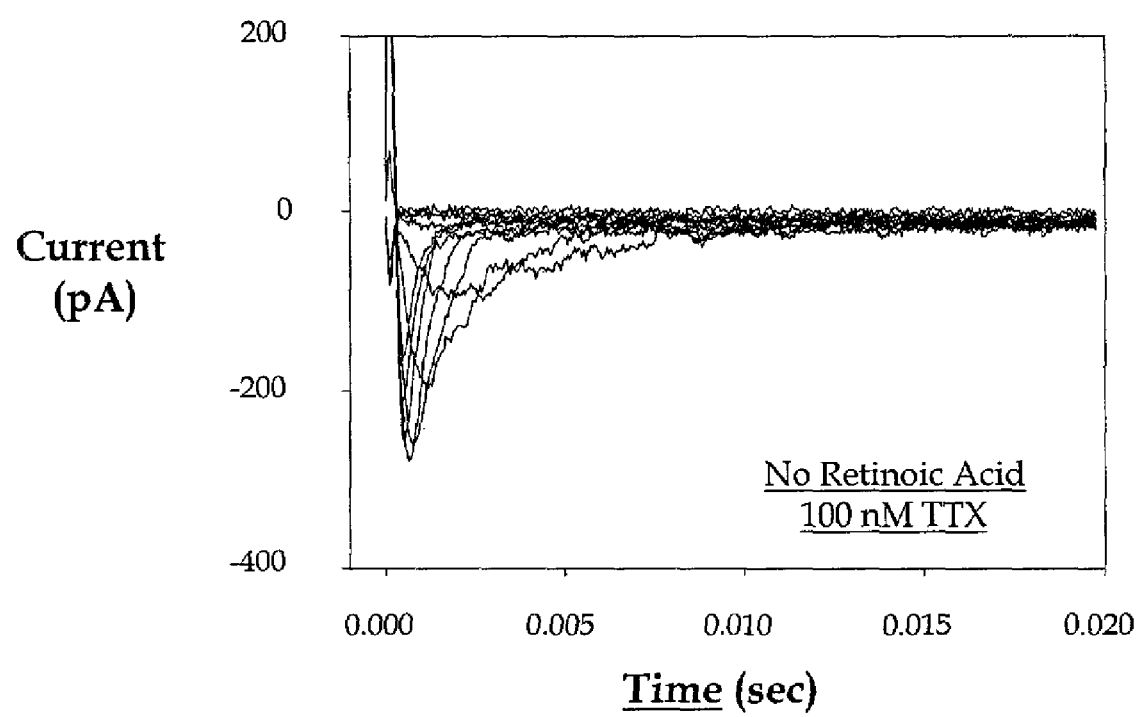
Figure 8:
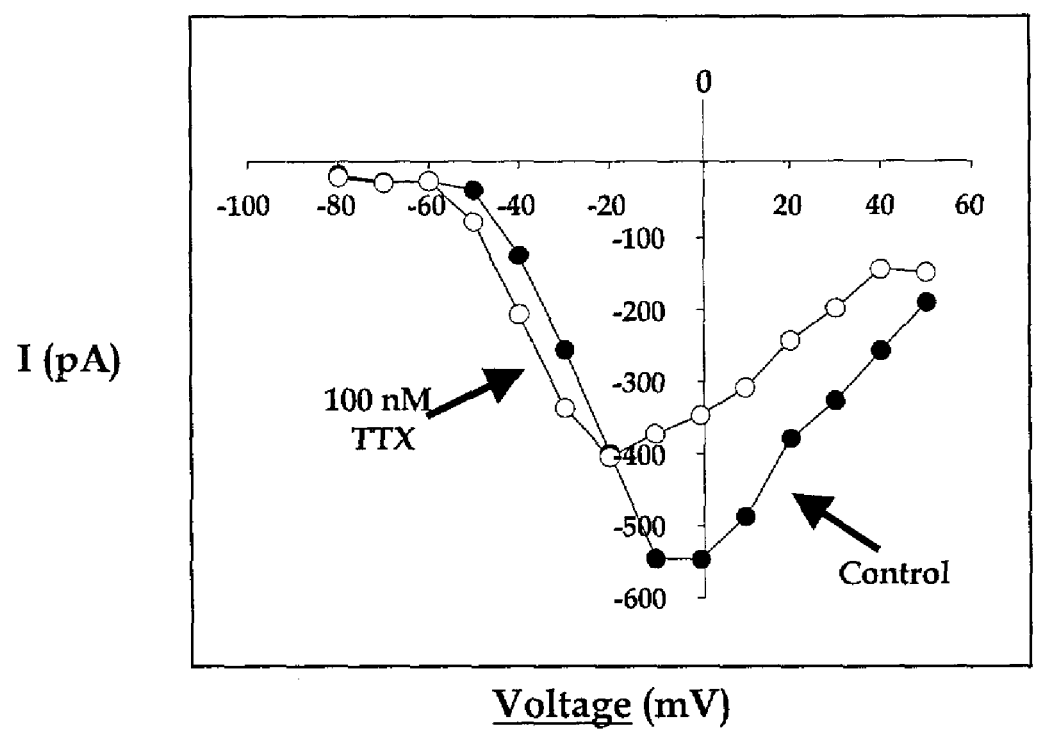
Figure 8:
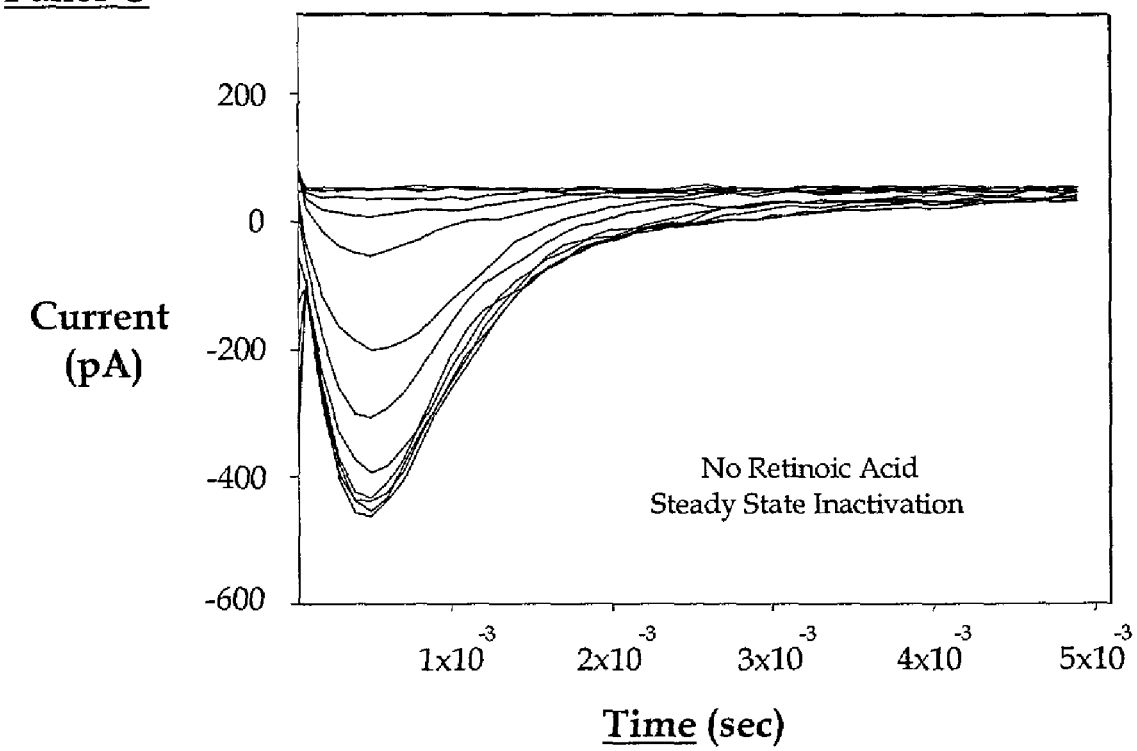
Figure 8:
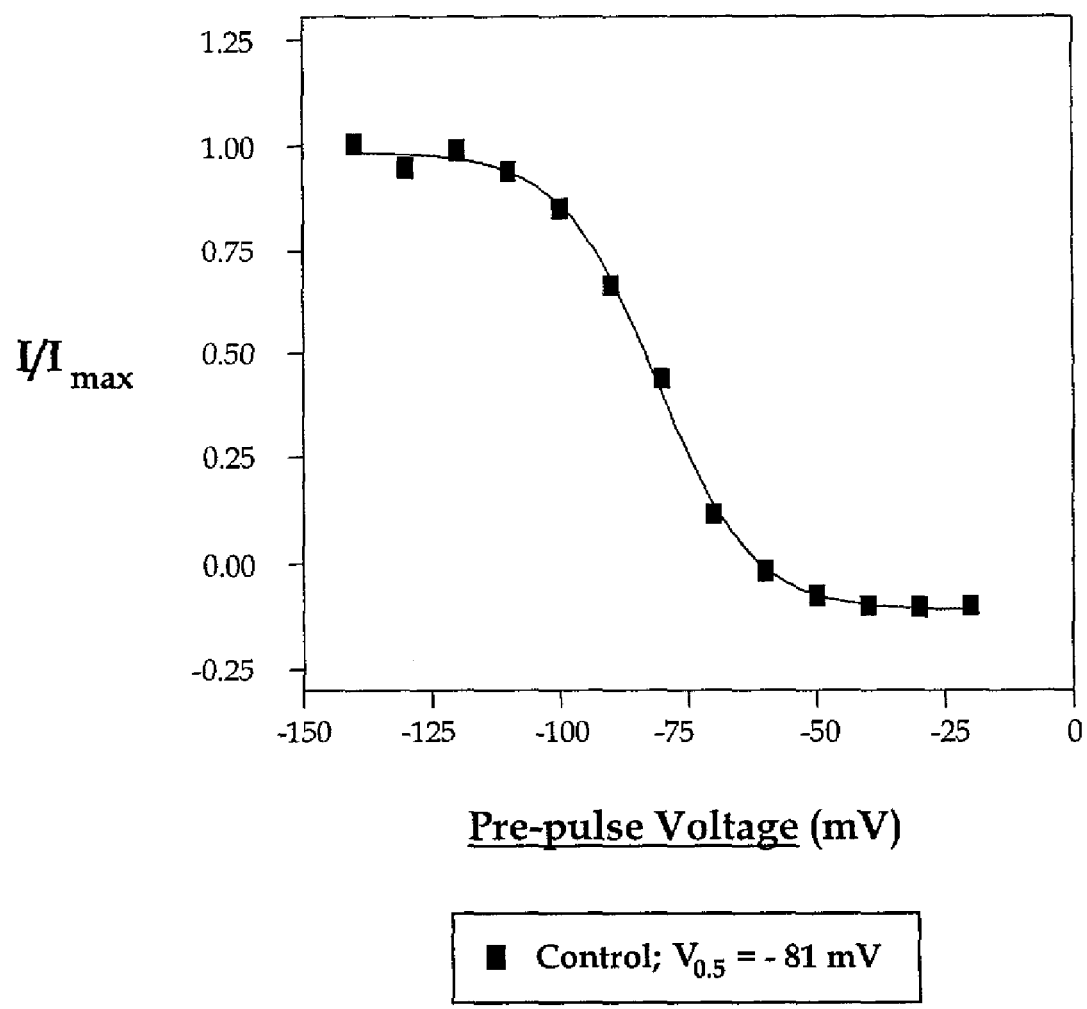

FIG. 8, Panels A, B, C and D: IMR-32 cells grown in the absence of RA were only partially blocked by TTX (100 nM). Cells were tested under conditions in which Ca currents would be observed if present.

Panel A: Families of voltage activated currents was elicited by voltage steps according to the protocol described in the previous figures from a cell in the absence (left) and presence (right) of TTX.

Panel B: TTX (100 nM) slightly blocked the inward currents elicited in this cell and shifted the voltage dependence of activation to the left.

Panel C: Steady state inactivation in the absence of TTX was determined according to the protocol described in FIG. 5.

Panel D: The voltage dependence of steady state inactivation under control conditions revealed an inactivating current with $V_{0.5}$=−81 mV.

Figure 9:
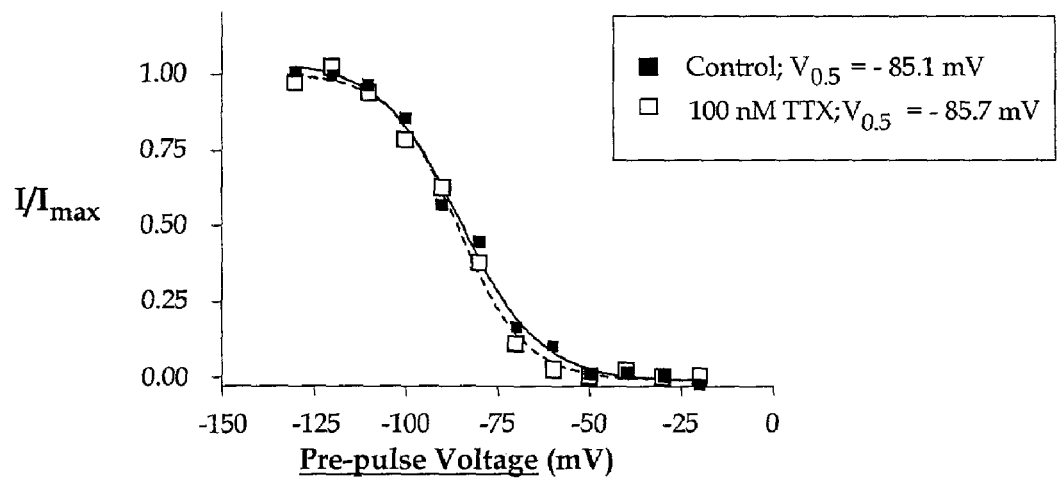
Figure 9:
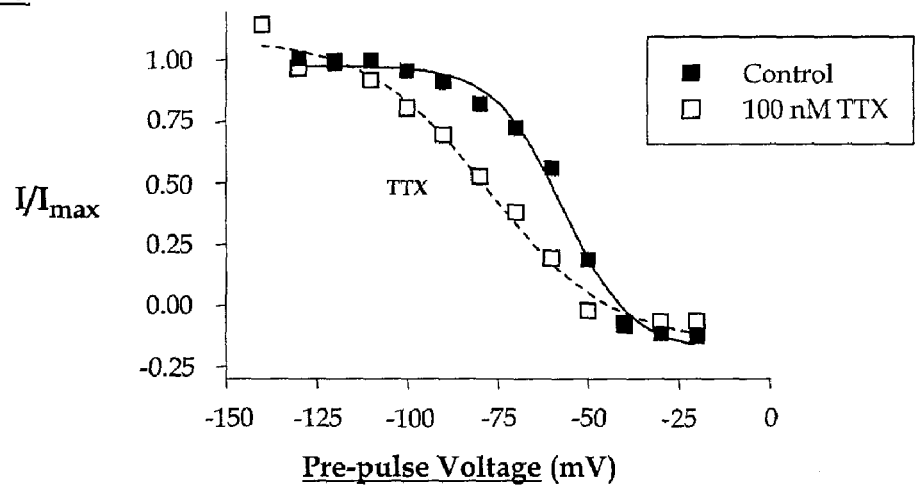

FIG. 9, Panels A, B, and C:

Panel A: The proportion of TTX-sensitive inward currents expressed in IMR-32 cells grown with RA (solid black squares) was directly related to the proportion of inward currents having a depolarized $V_{0.5}$ for steady state inactivation. IMR-32 cells grown in the absence of RA expressed TTX-R currents with $V_{0.5}$~−85 mV. IMR-32 RA+ cells expressing large TTX-S currents were those that revealed a voltage dependence of steady state inactivation similar to that reported for SCN3a recombinant channels (~−65 mV (Cummins et al. (2001)), 70 mV (Chen et al. (2000)).

Panel B: The electrophysiological characteristics of the current in cells that do not have a preponderance of Nav1.3 ion channels is shown.

Panel C: The electrophysiological characteristics of the current in cells that is consistent with expression of Nav1.3 ion channels is shown.

DETAILED DESCRIPTION OF THE INVENTION

The present invention provides methods to identify compounds that modulate the function of endogenously expressed ion channels, including, but not limited to, $Na_v1.3$ and $Na_v1.7$. The present invention provides IMR-32 cells differentiated by 9-cis RA predominantly expressing $Na_v1.3$ and thus, are ideally suited to identify compounds that modulate $Na_v1.3$ function.

Accordingly, we approached this challenge by first determining whether $Na_v1.3$ and $Na_v1.7$ function could be effectively studied in a stable cell line. Specifically, we examined $Na_v1.3$ and $Na_v1.7$ function in the human neuroblastoma cell line, IMR-32, under different growth conditions. The IMR-32 neuroblastoma cell line (ATCC #CCL-127) was established by W. W. Nichols, J. Lee and S. Dwight in April, 1967 from an abdominal mass occurring in a 13-month-old Caucasian male (Tumilowicz et al., "Definition of a Continuous Human Cell Line Derived from Neuroblastoma", *Cancer Res.* (1970) 30:2110–2118). The tumor was diagnosed as a neuroblastoma with rare areas of organoid differentiation and the cell line contains two cell types: a small neuroblast-like cell (predominant) and a large hyaline fibroblast. Initially, DNA microarray analysis was used to identify IMR-32 as a cell line that potentially expressed $Na_v1.3$ and $Na_v1.7$. Through the use of quantitative PCR, electrophysiological recordings and $Na_v1.3$ and $Na_v1.7$ specific antibodies, we demonstrated that IMR-32 cells do, in fact, express endogenous TTX-sensitive inward currents and predominantly $Na_v1.3$ mRNA when cultured in the presence of RA (1 μM) or predominantly $Na_v1.7$ mRNA when cultured without RA (1 μM). Nav1.3 and Nav1.7 were detected in Western blot analysis indicating the translation into protein in this line under different culture conditions. Thus, both RA-differentiated and undifferentiated IMR-32 cells are ideal for use in vitro assays designed to investigate human $Na_v1.3$ and $Na_v1.7$ function. As such, this allows a target driven approach to be taken with regard to $Na_v1.3$ and $Na_v1.7$ drug discovery.

Candidate compounds identified using the methods of the present invention are also useful for treating diseases and conditions mediated by $Na_v1.3$ and $Na_v1.7$ including, but not limited to, neuropathic pain, chronic pain, anxiety, seizure, epilepsy (up-regulation in epileptic hippocampus tissue (Whitaker et al. (2001)), ischemia, migraine, bipolar disorder, deafness, schizo-affective disorder, Alzheimer's disease, stroke, Parkinson's disease, tinnitus, depression and substance abuse, asthma and chronic stress, prostate cancer and other cancerous tissues expressing high levels of Nav1.3 and Nav1.7. Compounds are administered to a subject in need thereof as an active ingredient in a suitable pharmaceutical composition.

The compounds of the present invention may be any type of organic or inorganic substances, including, but not limited to, proteins, peptides, antibodies, small organic molecules and inorganic molecules.

Pharmaceutically useful compositions comprising modulators of $Na_v1.3$ and/or $Na_v1.7$ activity, may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, or modulator compound.

The pharmaceutical compositions of the present invention can be prepared according to conventional pharmaceutical techniques. A pharmaceutically acceptable carrier may be used in the compositions of the present invention. A wide variety of pharmaceutical compositions are suitable for use in the present invention. It is readily apparent to those skilled in the art that different compositions may be used depending on the route of administration including, but not limited to, intravenous (both bolus and infusion), oral, nasal, pulmonary, transdermal, topical with or without occlusion, intraperitoneal, intracranially, epidurally, directly into CSF, subcutaneous, intramuscular, intrathecal, ocular, or parenteral, all well known to those of ordinary skill in the pharmaceutical arts. In preparing the compositions in oral dosage form, one or more of the usual pharmaceutical carriers may be employed, such as water, glycols, oils, alcohols, flavoring agents, preservatives, coloring agents, syrup and the like in the case of oral liquid preparations (for example, suspensions, elixirs and solutions), or carriers such as starches, sugars, diluents, granulating agents, lubricants, binders, disintegrating agents and the like in the case of oral solid preparations (for example, powders, capsules and tablets).

Alternatively, the compounds may be administered parenterally via injection of a formulation consisting of the active ingredient dissolved in an inert liquid carrier. Acceptable liquid carriers include vegetable oils such as peanut oil, cotton seed oil, sesame oil, and the like, as well as organic solvents such as solketal, glycerol formal, and the like. As an alternative, aqueous parenteral formulations may also be used. For example, acceptable aqueous solvents include water, Ringer's solution and an isotonic aqueous saline solution. Further, a sterile, non-volatile oil can usually be employed as solvent or suspending agent in the aqueous formulation. The formulations are prepared by dissolving or suspending the active ingredient in the liquid carrier such that the final formulation contains from 0.005 to 10% by weight of the active ingredient. Other additives including a preservative, an isotonizer, a solubilizer, a stabilizer and a pain-soothing agent may adequately be employed.

The compounds may be administered ocularly via application of a formulation consisting of the active ingredient dissolved in an inert aqueous liquid carrier. Such aqueous liquid formulations are useful, for example, in the treatment of diabetic retinopathy. Acceptable aqueous solvents include water, Ringer's solution, and an isotonic aqueous saline solution. The formulations are prepared by dissolving or suspending the active ingredient in the liquid carrier such that the final formulation contains from 0.005 to 10% by weight of the active ingredient. Other additives including a preservative, an isotonizer, a solubilizer, a stabilizer and a pain-soothing agent may adequately be employed.

The compounds of the present invention may also be administered in the form of liposome delivery systems, such as small unilamellar vesicles, large unilamellar vesicles and multilamellar vesicles. Liposome delivery systems, are well known in the art, and may be formed from a variety of phospholipids, such as cholesterol, stearylamine or phosphatidylcholines.

As used herein, a "therapeutically effective amount" of the instant pharmaceutical composition, or compound therein, means an amount that is effective in treating a disease or condition medicated at least in part by $Na_v1.3$ and/or $Na_v1.7$, neuropathic pain, chronic pain, anxiety, seizure, epilepsy, ischemia, migraine, bipolar disorder, deafness, schizo-affective disorder, Alzheimer's disease, stroke, Parkinson's disease, tinnitus, depression and substance abuse, prostate cancer, asthma, and chronic stress. The instant pharmaceutical composition will generally contain a per dosage unit (e.g., tablet, capsule, powder, injection, teaspoonful and the like) from about 0.001 to about 100 mg/kg. In one embodiment, the instant pharmaceutical composition contains a per dosage unit of from about 0.01 to about 50 mg/kg of compound, but preferably from about 0.05 to about 20 mg/kg. Methods are known in the art for determining therapeutically effective doses for the instant pharmaceutical composition. The effective dose for administering the pharmaceutical composition to a human, for example, can be determined mathematically from the results of animal studies. Furthermore, compounds of the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

Oral Dosage Forms

Because of their ease of administration, tablets and capsules represent an advantageous oral dosage unit form, wherein solid pharmaceutical carriers are employed. If desired, tablets may be sugar-coated or enteric-coated by standard techniques. For liquid forms, the active drug component can be combined in suitably flavored suspending or dispersing agents such as the synthetic and natural gums, for example, tragacanth, acacia, methyl-cellulose and the like. Other dispersing agents that may be employed include glycerin and the like.

The present invention is also directed to methods for screening test compounds that are suspected of being able to modulate the expression of DNA or RNA encoding $Na_v1.3$ and/or $Na_v1.7$ as well as the function of the $Na_v1.3$ and/or $Na_v1.7$ ion channels in vitro or in vivo. Compounds that modulate these activities may include but are not limited to DNA, RNA, peptides, proteins, or non-proteinaceous organic or inorganic molecules. Compounds may modulate by increasing or attenuating the expression of DNA or RNA encoding $Na_v1.3$ and/or $Na_v1.7$, or the function of the $Na_v1.3$ and/or $Na_v1.7$ ion channels. Compounds that modulate the expression of DNA or RNA encoding $Na_v1.3$ and/or $Na_v1.7$ or the function of $Na_v1.3$ and/or $Na_v1.7$ protein may be detected by a variety of assays utilizing cells or fractions and components thereof, prepared according to the methods disclosed in present specification or standard methods well known to those skilled in the art. The assay may be a simple "yes/no" assay to determine whether there is a change in expression, ligand binding, or function of the target molecule. The assay may be made quantitative by comparing the expression, ligand binding or function of the target molecule in the presence of a test sample with the levels of expression, ligand binding, or function of the target molecule in a standard or control sample. Modulators identified in this process are useful as therapeutic agents, research tools, and diagnostic agents. Such modulators can include agonists, antagonists, and inverse agonists of the $Na_v1.3$ and/or $Na_v1.7$ ion channels.

It is to be understood that this invention is not limited to the particular methodologies, protocols, constructs, formulae and reagents described and as such may vary. It is also to be understood that the terminology used herein is for the purpose of describing particular embodiments only, and is not intended to limit the scope of the present invention.

It must be noted that as used herein and in the appended claims, the singular forms "a," "an," and "the" include plural reference unless the context clearly dictates otherwise. Thus, for example, reference to "a gene" is a reference to one or more genes and includes equivalents thereof known to those skilled in the art, and so forth.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are incorporated herein by reference for the purpose of describing and disclosing, for example, the constructs and methodologies that are described in the publications, which might be used in connection with the presently described invention. Nothing herein is to be construed as an admission that the inventor is not entitled to antedate such disclosure by virtue of prior invention.

The following Examples are provided for the purpose of illustrating the present invention, without, however, limiting the present invention to the specific disclosure contained in the following Examples.

EXAMPLE 1

Exposure Of IMR-32 Cells to RA Alters the Expression of a Populations of TTX-S Sodium Channel Alpha Subunits Revealing an Up-Regulation of $Na_v1.3$ and Down-Regulation Of $Na_v1.7$ mRNA Cell Culture IMR-32 cells (American Tissue Culture Collection #CCL-127, Manassas, Va.), stored at −140° C. in freezing media (90% fetal bovine serum, 10% DMSO), were rapidly-thawed at 37° C., washed in normal IMR-32 medium (Eagle's minimum essential media containing Hanks balanced salts, 1.5 gram/liter sodium bicarbonate, 1 mM sodium pyruvate, 0.1 mM non-essential amino acids, 2 mM L-glutamine, 10% fetal bovine serum) to remove the DMSO and centrifuged at 1000 rpm for two minutes at 4° C. to pellet the cells. The cell pellet was re-suspended in fresh IMR-32 medium, plated in a 150 $cm^2$ tissue culture flask and incubated at 37° C. in 5% $CO_2$ until confluent. Confluent cells were washed in calcium-free phosphate buffer, treated with 0.02% trypsin until dislodged and serially-passed into 150 $cm^2$ tissue culture flasks containing IMR-32 media supplemented with 9-cis RA to 1 μM final concentration and incubated as above. Initially, IMR-32 cells cultured in 9-cis RA proliferated slowly. Following a three-week culture in RA, the cells stabilized and were passed 1:2 to maintain robust proliferation. Cells destined for use in the fluorescence assay were passed using calcium-free buffer (Versene; Gibco) to ensure retention of TTX sensitivity.

Figure 3:
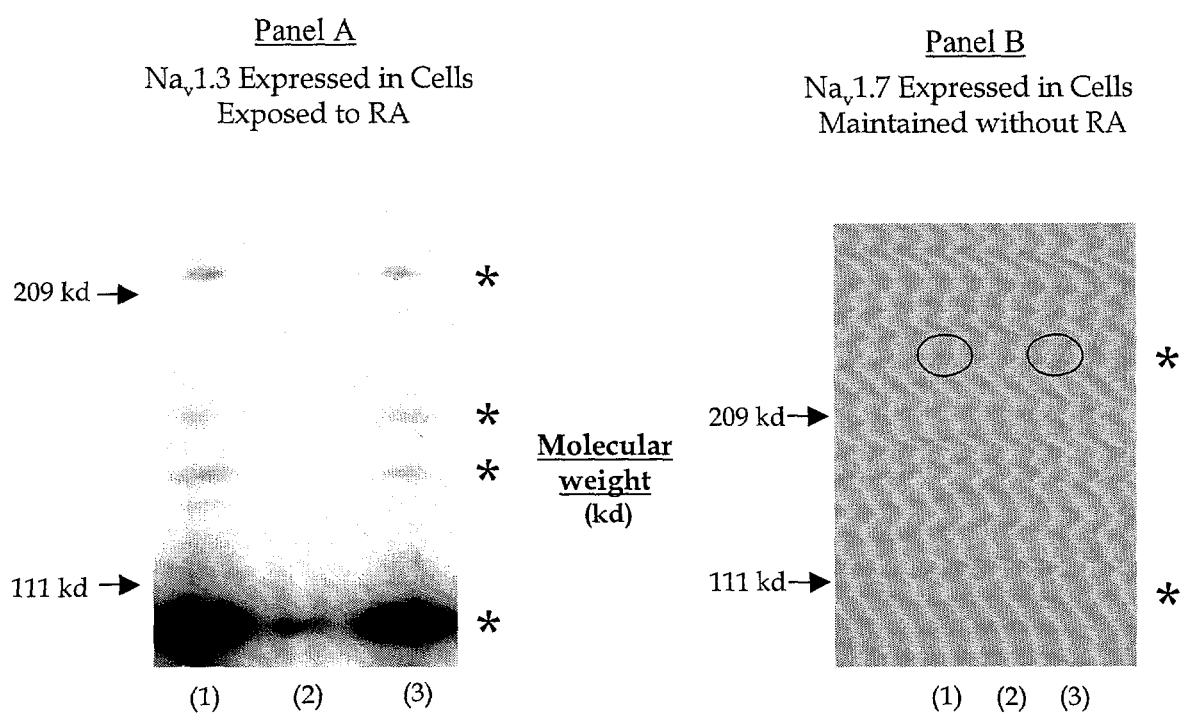
FIG. 3, Panels A and B: Western immunoblot detection of $Na_v1.3$ and $Na_v1.7$ expression in IMR 32 cells maintained under different growth conditions.

PCR-based screening of IMR-32 cells was done to determine mRNA levels of alpha and beta sodium channel subunits. Quantitative PCR was used to determine relative expression of TTX-sensitive voltage-gated sodium channels in IMR-32 cells since veratridine-induced depolarization was completely suppressed by 100 nM TTX (FIG. 3). For this procedure, IMR-32 cells were grown in 10 $cm^2$ culture dishes until 80% confluent; whereupon, total RNA was isolated from the cells with Trizol reagent (Gibco) as per the manufacturer's protocol. Following spectrophotometric quantification, 1.5 μg of total RNA, isolated from IMR-32 cells grown either in the presence or absence of 9-cis RA (1 µM) were reverse-transcribed into cDNA with Superscript II reverse transcriptase (Gibco) as per the manufacturer's protocol. Synthesized cDNAs were diluted 1:4 in nuclease-free $H_2O$ supplemented with poly-inosine to a final concentration of 50 nanograms per milliliter, heated at 70° C. for five minutes and placed on ice for an additional two minutes. Primers that span putative introns were used in PCR experiments to permit positive identification of amplicons synthesized from cDNA templates.

```
Primer sequences included:
Na_v 1.1
(Forward) 5' CAA AAG CCT ATA CCT CGA CCA 3'       SEQ ID NO:1
(Reverse) 5' TCA GCT CGG CAA GAA ACA TAC 3'       SEQ ID NO:2

Na_v 1.2
(Forward) 5' ACT GGT TAG CTT AAC TGC AAA TGC CTT GG 3'  SEQ ID NO:3
(Reverse) 5' ACG CTT ACA TCA AAC ATC TCT CCA GTG G 3'   SEQ ID NO:4

Na_v 1.3
(Forward) 5' TTG GAA GAA GCA GAA CAA AAA GAG G 3'       SEQ ID NO:5
(Reverse) 5' AGG GGA GCA GAA TTT TTT GTC ACT GG 3'      SEQ ID NO:6

Na_v 1.4
(Forward) 5' TCT CAG AGC CTG AGG ATA GCA 3'       SEQ ID NO:7
(Reverse) 5' AAT GAC TCG CCG CTG CTC AAT 3'       SEQ ID NO:8

Na_v 1.6
(Forward) 5' TTG GAG TAT TTC TCC CTC TGA G 3'     SEQ ID NO:9
(Reverse) 5' ATG CAG CTT CAG TAT ACA TTC CA 3'    SEQ ID NO:10

Na_v 1.8
(Forward) 5' TGT GGA ACA GCC TGA GGA ATA CTT GG 3'  SEQ ID NO:11
(Reverse) 5' TGG AGG GGA TGG CGC CCA CCA AGG 3'     SEQ ID NO:12

Na_v 1.9
(Forward) 5' ATC CCT TCG GAC ACT GAG AGC TTT AAG ACC 3'  SEQ ID NO:13
(Reverse) 5' TGG GCT GCT TGT CTA CAT TAA CAG AAT CC 3'   SEQ ID NO:14
```

Figure 1:
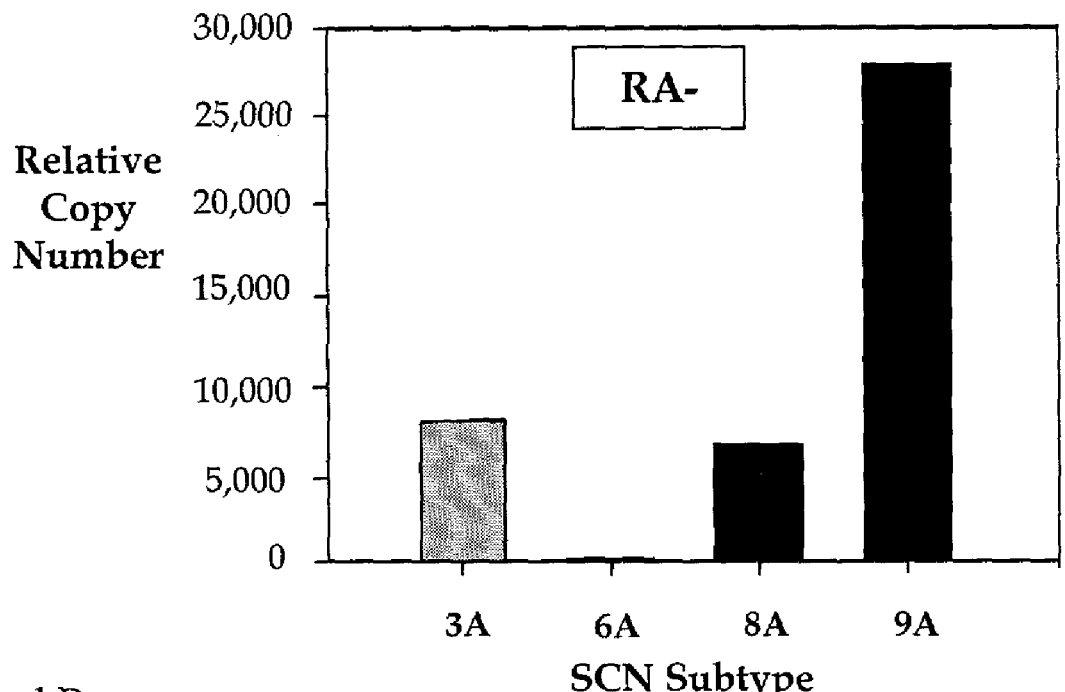
FIG. 1, Panels A and B: Quantitative PCR data showing the effects of RA on the relative expression of $Na_v$ mRNA.
  Panel A: Predominant expression of $Na_v1.7$ mRNA was observed in IMR-32 cells cultured without 9-cis-RA.
  Panel B: 9-cis-RA (1 μM) induced up-regulation of $Na_v1.3$ mRNA and down-regulation of $Na_v1.7$ mRNA expression.
Figure 1:
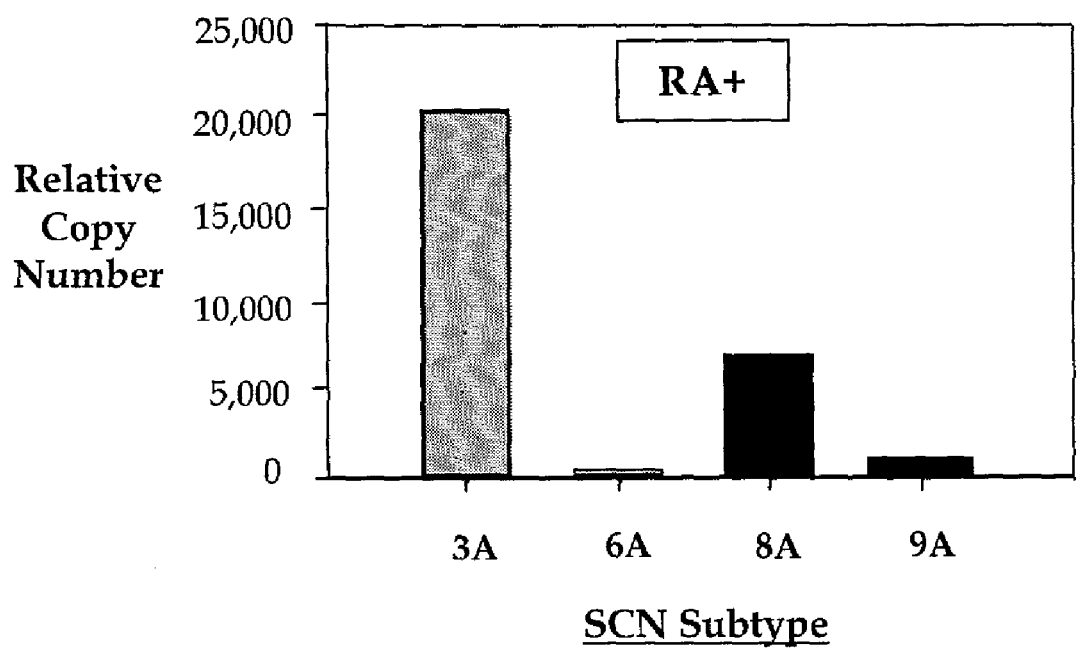
Figure 2:
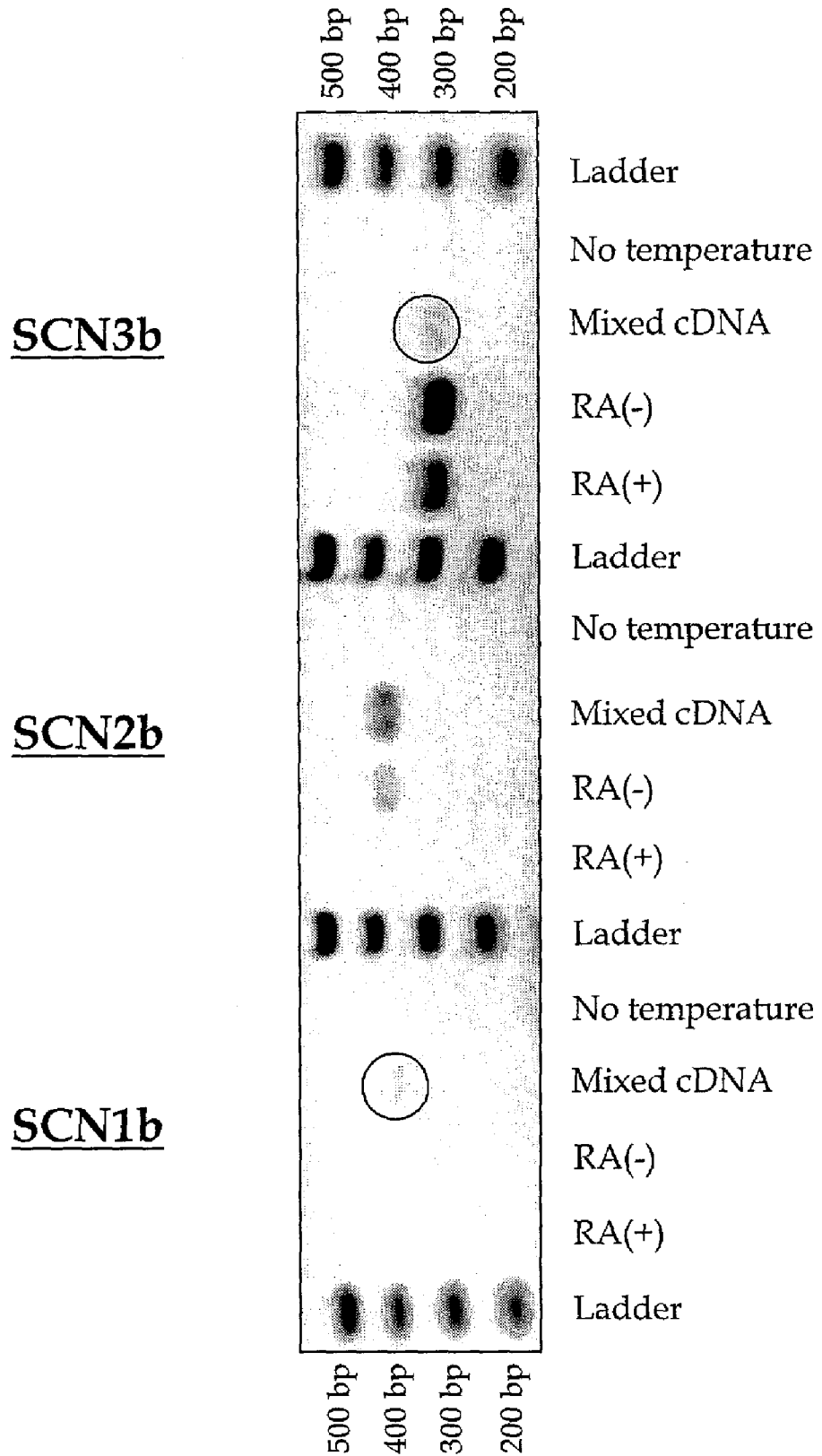
FIG. 2: PCR determination of SCN beta subunit expression in IMR-32 cells cultured with (rRA+) and without (RA−) 9-cis RA (1 μm). Mixed cDNA (human brain, skeletal muscle and heart; invitrogen) served as a positive control for RT-PCR experiments. Intron-spanning oligonucleotides were used to distinguish cDNA-derived amplicons.

Amplicons were fractionated by ethidium bromide agarose gel electrophoresis and visualized under ultraviolet light. Amplicons of the predicted molecular weight were subcloned into the pCR4-TOPO TA cloning vector (Invitrogen, Carlsbad, Calif.) as per the manufacturer's protocol and sequenced. Relative TTX-sensitive $Na_v$ expression in IMR-32 cells was determined by quantitative PCR using sequence-positive plasmids as standards. As shown in FIG. 1, expression of $Na_v1.7$ (SCN9a) mRNA predominates in undifferentiated IMR-32 cells. IMR-32 cells cultured for more than three weeks in 1 µM 9-cis RA predominantly express $Na_v$ 1.3 mRNA with concomitant down-regulation of $Na_v1.7$ (Panel B). $Na_v1.1$, $Na_v1.2$, $Na_v1.4$ and $Na_v1.6$ mRNA were not detected by RT-PCR.

Expression of Na channel beta subunits 1 to 3 in IMR-32 cells grown with or without RA was determined using non-quantitative RT-PCR.

```
Primer sequences were:
SCN1b
                                                  SEQ ID NO:15
(Forward)   5' ACGCTGAGACCTTCACCGAGT 3'

SEQ ID NO:16
(Reverse)   5' ACCACAACACCACAATGAGCAC 3'

SCN2b
                                                  SEQ ID NO:17
(Forward)   5' GACTAACATCTCAGTCTCTGAAAAT 3'

SEQ ID NO:18
(Reverse)   5' GGCTGCACGTTTCTCAGCATCA 3'

SCN3b
                                                  SEQ ID NO:19
(Forward)   5' TGACTACCTTGCCATCCCATCT 3'

SEQ ID NO:20
(Reverse)   5' CTTCTCAGTTCTGGCAGAGTCTTA 3'
```

Mixed cDNA (human brain, skeletal muscle and heart; Invitrogen) served as a positive control for PCR experiments. Intron-spanning oligonucleotides were used to distinguish cDNA-derived amplicons. Beta3, but not beta1 and beta2, was detected in IMR-32 cells exposed to RA. Beta2 and beta3 were detected in cells not exposed to RA.

EXAMPLE 2

Cell-Based Assay Using Voltage Sensitive Dyes to Measure $Na_v$ Activity in IMR-32 Cells IMR-32 cells cultured in growth medium (Eagles minimal essential media, 2 mM L-glutamine and Earle's BSS adjusted to contain 1.5 g/L sodium bicarbonate, 0.1 mM non-essential amino acids, 1.0 mM sodium pyruvate, 1 µM RA) are plated (40 µl per well) at a density of $5.5\times10^6$ cells per 384-well plate and incubated for eighteen to twenty-four hours at approximately 37° C. in 5% $CO_2$. IMR-32 cells were plated on tissue culture-treated plates without poly-D-Lysine since prolonged exposure to poly-D-lysine (e.g. commercially prepared cell culture plates) reduced cell adhesion and viability. The saline used in most studies was 2K/2 Ca buffer, and it contained (in mM): 130 mM NaCl, 2 mM KCl, 1 mM $MgCl_2$, 2 mM $CaCl_2$, 20 mM HEPES, pH 7.4. On the day of the assay, 20× voltage-sensitive dye (Molecular Devices, Sunnyvale, Calif.; catalog # R8034) was diluted 1:10 in 2K/2 Ca saline supplemented with barium chloride (250 µM final concentration for $Na_v1.3$ expressing cells; 375 µM final concentration for predominantly $Na_v1.7$-expressing cells) and added (40 µl per well) to the cells without mixing. The cells were incubated in voltage-sensitive dye for five to sixty minutes at room temperature in the dark; whereupon, the cells were challenged on-line with test compounds suspected of having $Na_v1.3$ and/or $Na_v1.7$ modulating activity, using a fluorometric imaging plate reader (FLIPR™) for compound addition and data collection. In this assay, 13 µl of each test compound (170 µM initial) were added with mixing (10 µl/sec) to each well and incubated for six minutes. Subsequently, 5 µl of 200 µM veratridine ($Na_v$ 'activator') were added with mixing (15 µl/sec) to each well to achieve a final veratridine concentration of 10 µM. Cell fluorescence was monitored for an additional 70 seconds. Depolarization elicited by the influx of $Na^+$ ions produced an increase in fluorescence. The observed depolarization induced by veratridine was dependent on external $Na^+$. The screening window index W [where W=3 * (sd unblocked signal+sd blocked signal)/(unblocked mean signal−blocked mean signal)] was determined by including 100 nM TTX in half the wells of a 384-plate with subsequent stimulation of all wells with veratridine. For this example, the W value ranged from 0.66 to 0.77.

FIG. 4, Panel A shows an example of veratridine-induced $Na_v$ activation following six minutes pre-incubation with either 2K/2 Ca saline (solid line) or 100 nM TTX (dashed line) in IMR-32 cells that had been maintained in RA. A dose-dependent block by the neurotoxin TTX was observed. The concentration to half block the veratridine-induced increase in fluorescence ($IC_{50}$)=2.8+/−0.3 nM (n=3 separate experiments, mean +/−SD) (FIG. 3, Panel B). Final DMSO concentrations up to 2% were tolerated. TTX blockade was also examined in IMR-32 cells grown without RA and the $IC_{50}$ was 2.6+/−0.6 nM (n=2) (FIG. 3, Panel C). The steepness of the dose response relationship appeared to be less in cultures grown without RA (1.0, 1.5) vs. with RA (0.76, 0.89 and 0.79). Furthermore, TTX had a tendency to completely block a greater proportion of the veratridine-induced response in cells that were maintained with RA (88, 89, 90%) compared to those grown in the absence of RA (82, 80%).

In another example, cells were washed with 0-Na solutions (150 mM TMA-Cl, 0.1 mM $CaCl_2$, 1.2 mM $MgCl_2$, 10 mM Dextrose, 10 mM HEPES free acid, pH to 7.4 using CsOH), incubated in CC2 (Aurora Bioscience) for 30 min and subsequently in DiSBAC2 (Aurora Bioscience) together with veratridine, and assayed using ViPR™ technology. Addition of Na+-containing solution (similar volume) caused a depolarization of the membrane potential and decreased FRET between the CC2 and oxonol dyes. Antagonists were incubated together with veratridine/DiSBAC2. TTX produced dose dependent decreases in the FRET signal (data not shown).

EXAMPLE 3

Exposure of IMR-32 Cells to RA Alters the Expression of Populations of TTX-S Sodium Currents Consistent with an Up-Regulation of $Na_v1.3$.

Electrophysiological Recordings from IMR-32 Cells

The endogenous voltage gated Na currents expressed in IMR-32 cells grown in the presence or absence of 1 µM RA were measured using standard whole cell voltage clamp techniques (Hamill et al. (1981). The whole cell patch clamp technique was used to record voltage-activated currents from IMR-32 cells maintained for two or more days on 12 mm glass coverslips in the presence or absence of RA (1 µM). Cells were visualized using a Nikon Diaphot 300 with DIC Nomarski optics. The standard physiological saline (1 Ca tyrodes ("Tyrodes") contains: 130 mM NaCl, 4 mM KCl, 1 mM $CaCl_2$, 1.2 mM $MgCl_2$, and 10 mM hemi-Na-HEPES (pH 7.3, 295–300 mOsm as measured using a Wescor 5500 vapor-pressure (Wescor, Inc., Logan, Utah)). Recording electrodes are fabricated from borosilicate capillary tubing (R6; Garner Glass, Claremont, Calif.), the tips are coated with dental periphery wax (Miles Laboratories, South Bend, Ind.), and have resistances of 1 to 2 MΩ when containing an intracellular saline designed to block outward currents: 140 mM CsCl, 0.483 mM $CaCl_2$, 2 mM $MgCl_2$, 10 mM HEPES free acid and 1 mM $K_4$-BAPTA (100 nM free $Ca^{+2}$); pH 7.4, with dextrose added to achieve 290 mOsm). Current and voltage signals are detected and filtered at 2 kHz with an Axopatch 1D patch-clamp amplifier (Axon Instruments, Foster City, Calif.), digitally recorded with a DigiData 1200B laboratory interface (Axon Instruments) and PC compatible computer system and stored on magnetic disk for off-line analysis. Data acquisition and analysis are performed with PClamp software.

The total membrane capacitance ($C_m$) was determined as the difference between the maximum current after a 30 mV hyperpolarizing voltage ramp from −100 mV (generated at a rate of 10 mV/ms) and the steady state current at the final potential (−130 mV) (Dubin et al. (1999)).

Families of voltage-gated inward currents were obtained using a standard P/−4 protocol from −100 mV. Depolarizing voltage steps in increments of 10 mV were applied from a holding potential of −100 mV. Steady state inactivation was elicited by measuring the peak current at 0 mV after a 500 msec pre-pulse voltage between −140 and −20 mV in increments of 10 mV.

Cells grown for more than two weeks in RA and tested in Tyrodes revealed larger peak inward currents (−75.3+/−10.6 pA/pF (n=24) vs. −43.3+/−6.1 pA/pF (n=6)) compared to cells cultured without RA (p<0.02, Student's t test). The cell sizes were similar in the presence and absence of RA (10.2 vs. 11.6 pF; p=0.558). Cells were thoroughly rinsed in Tyrodes without RA prior to recording. Inward currents were reduced in low Na Tyrodes where TMA was substituted for the majority of Na (25 mM). Under the conditions used in these studies (with CsCl in the pipet) outward currents were blocked (FIGS. 5–8).

Inward currents elicited in IMR-32 cells grown in RA revealed heterogeneity in their sensitivity to bath applied TTX at 100 nM (FIGS. 5 and 7). The concentration of TTX chosen for the electrophysiological studies (100 nM) completely blocked the veratridine-induced fluorescence signal in the assay described in Example 3. In some cells, inward currents were substantially and reversibly blocked by TTX (FIG. 5). These cells had complex steady state inactivation curves and TTX blocked currents that inactivated only at depolarized potentials, having a voltage dependence $V_{0.5}$ consistent with that reported for the recombinant human SCN3a (−58 and −69 mV (Cummins et al. (2001)), and native rat sodium currents in axotomized small DRG neurons (−72 mV) (Cummins et al. (2001)). Inward currents in other cells from the same plating of IMR-32 cells with RA were largely TTX-R (FIG. 7). Interestingly, steady state inactivation relationships revealed that this latter population of cells lacked or expressed less of the inward component contributing to the depolarized $V_{0.5}$ (FIG. 7, Panels C and D) The voltage to half-inactivate the channels was near −85 mV. The molecular identity of the TTX-R inward current included, in large part, calcium currents since the TTX-R current could be blocked nearly completely by 500 µM $Cd^{2+}$ and in part by 5 µM mibefradil. $Cd^{2+}$ blocked 50+/−2% and 68+/−6% of the TTX-R current at 100 and 500 µM, respectively.

There was a strong correlation between the degree of TTX block and the magnitude of the inward current component with a depolarized steady state voltage to half inactivation ($V_{0.5}$) (FIG. 9 Panel A). Thus, inward currents that were largely TTX-S revealed a voltage dependence for steady state inactivation that was shifted to the right along the voltage axis, consistent with the functional expression of SCN3a channels.

The TTX-S component of inward currents expressed in IMR-32 cells not exposed to RA tended to be a smaller proportion of total current compared to that in RA-treated cells (17+/−6% (n=6) vs. 36+/−7(n=19)). Fast transient calcium currents contributed to the TTX-R component in cells cultured without RA as well. IMR-32 cells grown without RA expressed fast transient inward currents with a negative shifted voltage dependence of inactivation compared to sister cultures maintained in RA. The $V_{0.5}$ for steady state inactivation is similar to the values determined for PN1 (SCN9a, $Na_v1.7$) expressed in a recombinant expression system (Sangameswaran et al. (1997); Cummins et al. (1998)).

Thus, IMR-32 cells showed heterogeneity in their block by TTX in electrophysiological (FIGS. 5 to 8) assays. Since TTX nearly completely blocks the veratridine induced signal in both RA+ and RA− treated cells, the depolarization observed in the fluorescence assay requires activation of Nav but other secondary conductances may contribute if activated by the veratridine-induced depolarization.

References

1. Akopian et al., "Structure and Distribution of a Broadly Expressed Atypical Sodium Channel", *Febs Letters* (1997) 400(2):183–187.
2. Akopain et al., "TITLE", *Nat. Neurosci*, (1999) 2:541].
3. Amir et al., "Membrane Potential Oscillations in Dorsal Root Ganglion Neurons: Role in Normal Electrogenesis and Neuropathic Pain", *J. Neurosci.* (1999) 19(19):8589–8596.
4. Black et al., "Up-regulation of a Silent Sodium Channel After Peripheral, But Not Central, Nerve Injury in DRG Neurons", *J. Neurophysiol.* (1999) 82(5):2776–2785.
5. Black et al., "NGF has Opposing Effects on Na+Channel III and SNS Gene Expression in Spinal Sensory Neurons", *Neuroreport.* (1997) 8(9–10):2331–2335.
6. Black et al., "Spinal Sensory Neurons Express Multiple Sodium Channel: Alpha-subunit mRNAs", *Mol. Brain Res.* (1996) 43(1/2):117–131.
7. Boucher et al., "Potent Analgesic Effects of GDNF in Neuropathic Pain States", *Science (Washington, D. C.)* (2000) 290(5489):124–127.
8. Chabal et al., "The Effect of Intravenous Lidocaine, Tocainide, and Mexiletine on Spontaneously Active Fibers Originating in Rat Sciatic Neuromas", *Pain* (1989) 38(3):333–338.
9. Chahine et al., "Electrophysiological Characteristics of Cloned Skeletal and Cardiac Muscle Sodium Channels", *Am. J. Physiol.* (1996) 271(2, Pt. 2):H498–506.
10. Chaplan, Calcutt and Higuera, "TITLE", *J. Pain* (2001) 2(2):S1–21.
11. Chen et al., "Cloning, Distribution and Functional Analysis of the Type III Sodium Channel from Human Brain", *European Journal of Neuroscience* (2000) 12(12): 4281–4289.
12. Clare et al., "Voltage-Gated Sodium Channels as Therapeutic Targets", *Drug Discovery Today* (2000) 5(11): 506–520.
13. Coward et al., "Sodium Channel .Beta.1 and .Beta.2 Subunits Parallel SNS/PN3 .Alpha.-Subunit Changes in Injured Human Sensory Neurons", *NeuroReport* (2001) 12(3):483–488; "Plasticity of TTX-Sensitive Sodium Channels PN1 and Brain III in Injured Human Nerves", *NeuroReport* (2001) 12(3):495–500.
14. Cummins et al., "Nav1.3 Sodium Channels: Rapid Re-Priming and Slow Closed-State Inactivation Display Quantitative Differences After Expression in a Mammalian Cell Line and in Spinal Sensory Neurons", *J. Neurosci.* (2001) 21(16):5952–5961.
15. Cummins et al., "Slow Closed-State Inactivation: A Novel Mechanism Underlying Ramp Currents in Cells Expressing the HNE/PN1 Sodium Channel", *J. Neurosci.* (1998) 18(23):9607–9619.
16. T. R. Cummins and S. G. Waxman, "Down-regulation of Tetrodotoxin-Resistant Sodium Currents and Up-regulation of a Rapidly Re-priming Tetrodotoxin-Sensitive Sodium Current in Small Spinal Sensory Neurons After Nerve Injury", *Journal of Neuroscience* (1997) 17(10): 3503–3514.
17. Devor et al., "Systemic Lidocaine Silences Ectopic Neuroma and DRG Discharge Without Blocking Nerve Conduction", *Pain* (1992) 48(2):261–268.
18. Dib-Hajj et al., "Plasticity of Sodium Channel Expression in DRG Neurons in the Chronic Constriction Injury Model of Neuropathic Pain", *Pain* (1999) 83(3):591–600.
19. Diss et al., "Expression Profiles of Voltage-Gated Na(+) Channel Alpha-Subunit Genes in Rat and Human Prostate Cancer Cell Lines", *Prostate* (2001) 48(3):165–178.
20. Doyle et al., "The Structure of the Potassium Channel: Molecular Basis of K+Conduction and Selectivity", *Science (Washington, D. C.)* (1998) 280(5360):69–77.
21. Dubin et al., "Lysophosphatidic Acid Stimulates Neurotransmitter-Like Conductance Changes that Precede GABA and L-Glutamate in Early, Presumptive Cortical Neuroblasts", *J. Neurosci.* (1999) 19(4):1371–1381.
22. England et al., Peripheral Nerve Society Abstract (1999)
23. H. A. Fozzard and D. A. Hanck, "Structure and Function of Voltage-Dependent Sodium Channels: Comparison of Brain II and Cardiac Isoforms", *Physiol. Rev.* (1996) 76(3):887–926.
24. Goldin et al., "Nomenclature of Voltage-Gated Sodium Channels", *Neuron* (2000) 28(2):365–368.
25. S. Gurtu and P. A. Smith, "Electrophysiological Characteristics of Hamster Dorsal Root Ganglion Cells and their Response to Axotomy", *Journal of Neurophysiology* (1988) 59(2):408–423.
26. Hamill et al., "Improved Patch-Clamp Techniques for High-Resolution Current Recording from Cells and Cell-Free Membrane Patches", *Pflugers Archiv. European Journal of Physiology* (1981) 391(2):85–100.
27. L. L. Isom, "Pathobiology of Visceral Pain: Molecular Mechanisms and Therapeutic Implications I: Cellular and Molecular Biology of Sodium Channel .Beta.-subunits-Therapeutic Implications for Pain?", *Am. J. Physiol.* (2000) 278(3, Pt. 1):G349–353.
28. L. L. Isom, "Sodium Channel Beta. subunits: Anything but Auxiliary", *Neuroscientist* (2001) 7(1):42–54.

29. S. H. Kim and J. M. Chung, "An Experimental Model for Peripheral Neuropathy Produced by Segmental Spinal Nerve Ligation in the Rat", *Pain* (1992) 50(3):355–363.
30. O. Matzner and M. Devor, "Hyperexcitability at Sites of Nerve Injury Depends on Voltage-Sensitive Na+ Channels", *J. Neurophysiol.* (1994) 72(1):349–359.
31. Oh et al., "Na+ Channel .Beta.1 Subunit mRNA: Differential Expression in Rat Spinal Sensory Neurons", *Mol. Brain Res.* (1995) 30(2):357–361.
32. N. W. Plummer and M. H. Meisler, "Evolution and Diversity of Mammalian Sodium Channel Genes", *Genomics* (1999) 57(2):323–331.
33. Sangameswaran et al., "A Novel Tetrodotoxin-Sensitive, Voltage-Gated Sodium Channel Expressed in Rat and Human Dorsal Root Ganglia", *J. Biol. Chem.* (1997) 272(23):14805–14809.
34. Shah et al., ".Beta.3, A Novel Auxiliary Subunit for the Voltage Gated Sodium Channel is Up-regulated in Sensory Neurones Following Streptozocin Induced Diabetic Neuropathy in Rat", *Neurosci. Lett.* (2001) 309(1):1–4.
35. Sotgiu et al., "Effect of Systemic Lidocaine on Dorsal Horn Neuron Hyperactivity Following Chronic Peripheral Nerve Injury in Rats", *Somatosensory and Motor Research* (1992) 9(3):227–233.
36. D. L. Tanelian and M. B. MacIver, "Analgesic Concentrations of Lidocaine Suppress Tonic A-Delta and C Fiber Discharges Produced by Acute Injury", *Anesthesiology* (1991) 74(5):934–936.
37. Toledo Aral et al., "Identification of PN1, a Predominant Voltage-Dependent Sodium Channel Expressed Principally in Peripheral Neurons", *P.N.A.S., U.S.A.* (1997) 94(4):1527–1532.
38. Tumilowicz et al., "Definition of a Continuous Human Cell Line Derived from Neuroblastoma", *Cancer Res.* (1970) 30:2110–2118
39. S. G. Waxman, "The Molecular Pathophysiology of Pain: Abnormal Expression of Sodium Channel Genes and its Contributions to Hyperexcitability of Primary Sensory Neurons", *Pain* (1999) (Sup. 6):S133–140.
40. Waxman et al., "Type III Sodium Channel mRNA is Expressed in Embryonic but not Adult Spinal Sensory Neurons, and is Re-expressed Following Axotomy", *Journal of Neurophysiology* (1994) 72(1):466–470.
41. Whitaker et al., "Changes in the mRNAs Encoding Voltage-Gated Sodium Channel Types II and III in Human Epileptic Hippocampus", *Neuroscience (Oxford, U.K.)* (2001) 106(2):275–285.

What is claimed is:

1. A method for identifying a compound that increases $Na_v1.7$ ion channel activity comprising contacting IMR-32 cells expressing the $Na_v1.7$ ion channel with a compound in the presence of a $Na_v1.7$ ion channel antagonist and measuring an increase in sodium ion influx in the IMR-32 cells.

2. The method of claim 1 wherein said antagonist comprises tetrodotoxin or a local anesthetic.

3. The method of claim 2 wherein said local anesthetic is lidocaine.

* * * * *

SEQUENCE LISTING

```
<160> NUMBER OF SEQ ID NOS: 20

<210> SEQ ID NO 1
<211> LENGTH: 21
<212> TYPE: DNA
<213> ORGANISM: Artificial Sequence
<220> FEATURE:
<223> OTHER INFORMATION: Primer Oligonucleotide

<400> SEQUENCE: 1
caaaagccta tacctcgacc a                                                   21

<210> SEQ ID NO 2
<211> LENGTH: 21
<212> TYPE: DNA
<213> ORGANISM: Artificial Sequence
<220> FEATURE:
<223> OTHER INFORMATION: Primer Oligonucleotide

<400> SEQUENCE: 2
tcagctcggc aagaaacata c                                                   21

<210> SEQ ID NO 3
<211> LENGTH: 29
<212> TYPE: DNA
<213> ORGANISM: Artificial Sequence
<220> FEATURE:
<223> OTHER INFORMATION: Primer Oligonucleotide

<400> SEQUENCE: 3
actggttagc ttaactgcaa atgccttgg                                           29

<210> SEQ ID NO 4
<211> LENGTH: 28
<212> TYPE: DNA
<213> ORGANISM: Artificial Sequence
<220> FEATURE:
<223> OTHER INFORMATION: Primer Oligonucleotide
```

```
<400> SEQUENCE: 4
acgcttacat caaacatctc tccagtgg                              28

<210> SEQ ID NO 5
<211> LENGTH: 25
<212> TYPE: DNA
<213> ORGANISM: Artificial Sequence
<220> FEATURE:
<223> OTHER INFORMATION: Primer Oligonucleotide

<400> SEQUENCE: 5
ttggaagaag cagaacaaaa agagg                                 25

<210> SEQ ID NO 6
<211> LENGTH: 26
<212> TYPE: DNA
<213> ORGANISM: Artificial Sequence
<220> FEATURE:
<223> OTHER INFORMATION: Primer Oligonucleotide

<400> SEQUENCE: 6
aggggagcag aatttttgt cactgg                                 26

<210> SEQ ID NO 7
<211> LENGTH: 21
<212> TYPE: DNA
<213> ORGANISM: Artificial Sequence
<220> FEATURE:
<223> OTHER INFORMATION: Primer Oligonucleotide

<400> SEQUENCE: 7
tctcagagcc tgaggatagc a                                     21

<210> SEQ ID NO 8
<211> LENGTH: 21
<212> TYPE: DNA
<213> ORGANISM: Artificial Sequence
<220> FEATURE:
<223> OTHER INFORMATION: Primer Oligonucleotide

<400> SEQUENCE: 8
aatgactcgc cgctgctcaa t                                     21

<210> SEQ ID NO 9
<211> LENGTH: 22
<212> TYPE: DNA
<213> ORGANISM: Artificial Sequence
<220> FEATURE:
<223> OTHER INFORMATION: Primer Oligonucleotide

<400> SEQUENCE: 9
ttggagtatt tctccctctg ag                                    22

<210> SEQ ID NO 10
<211> LENGTH: 23
<212> TYPE: DNA
<213> ORGANISM: Artificial Sequence
<220> FEATURE:
<223> OTHER INFORMATION: Primer Oligonucleotide

<400> SEQUENCE: 10
atgcagcttc agtatacatt cca                                   23

<210> SEQ ID NO 11
<211> LENGTH: 26
```

```
<212> TYPE: DNA
<213> ORGANISM: Artificial Sequence
<220> FEATURE:
<223> OTHER INFORMATION: Primer Oligonucleotide

<400> SEQUENCE: 11
tgtggaacag cctgaggaat acttgg                                          26

<210> SEQ ID NO 12
<211> LENGTH: 24
<212> TYPE: DNA
<213> ORGANISM: Artificial Sequence
<220> FEATURE:
<223> OTHER INFORMATION: Primer Oligonucleotide

<400> SEQUENCE: 12
tggaggggat ggcgcccacc aagg                                            24

<210> SEQ ID NO 13
<211> LENGTH: 30
<212> TYPE: DNA
<213> ORGANISM: Artificial Sequence
<220> FEATURE:
<223> OTHER INFORMATION: Primer Oligonucleotide

<400> SEQUENCE: 13
atcccttcgg acactgagag ctttaagacc                                      30

<210> SEQ ID NO 14
<211> LENGTH: 29
<212> TYPE: DNA
<213> ORGANISM: Artificial Sequence
<220> FEATURE:
<223> OTHER INFORMATION: Primer Oligonucleotide

<400> SEQUENCE: 14
tgggctgctt gtctacatta acagaatcc                                       29

<210> SEQ ID NO 15
<211> LENGTH: 21
<212> TYPE: DNA
<213> ORGANISM: Artificial Sequence
<220> FEATURE:
<223> OTHER INFORMATION: Primer Oligonucleotide

<400> SEQUENCE: 15
acgctgagac cttcaccgag t                                               21

<210> SEQ ID NO 16
<211> LENGTH: 22
<212> TYPE: DNA
<213> ORGANISM: Artificial Sequence
<220> FEATURE:
<223> OTHER INFORMATION: Primer Oligonucleotide

<400> SEQUENCE: 16
accacaacac cacaatgagc ac                                              22

<210> SEQ ID NO 17
<211> LENGTH: 25
<212> TYPE: DNA
<213> ORGANISM: Artificial Sequence
<220> FEATURE:
<223> OTHER INFORMATION: Primer Oligonucleotide

<400> SEQUENCE: 17
```

```
gactaacatc tcagtctctg aaaat                                    25

<210> SEQ ID NO 18
<211> LENGTH: 22
<212> TYPE: DNA
<213> ORGANISM: Artificial Sequence
<220> FEATURE:
<223> OTHER INFORMATION: Primer Oligonucleotide

<400> SEQUENCE: 18
ggctgcacgt ttctcagcat ca                                       22

<210> SEQ ID NO 19
<211> LENGTH: 22
<212> TYPE: DNA
<213> ORGANISM: Artificial Sequence
<220> FEATURE:
<223> OTHER INFORMATION: Primer Oligonucleotide

<400> SEQUENCE: 19
tgactacctt gccatcccat ct                                       22

<210> SEQ ID NO 20
<211> LENGTH: 24
<212> TYPE: DNA
<213> ORGANISM: Artificial Sequence
<220> FEATURE:
<223> OTHER INFORMATION: Primer Oligonucleotide

<400> SEQUENCE: 20
cttctcagtt ctggcagagt ctta                                     24
```